United States Patent [19]

Kaye

[11] Patent Number: 4,526,470
[45] Date of Patent: Jul. 2, 1985

[54] STRAY LIGHT MEASUREMENT AND COMPENSATION

[75] Inventor: Wilbur I. Kaye, Corona del Mar, Calif.

[73] Assignee: Beckman Instruments, Inc., Fullerton, Calif.

[21] Appl. No.: 355,281

[22] Filed: Mar. 5, 1982

[51] Int. Cl.$^3$ .............................................. G01J 3/42
[52] U.S. Cl. .................................................... 356/319
[58] Field of Search ......................... 356/300, 319-325

[56] References Cited

PUBLICATIONS

Tarrant, "Optical Techniques for Studying Stray Light in Spectrophotometers", *Optica Acta*, vol. 25, No. 12, Dec. 1978, pp. 1167–1174.
"Standard Method of Estimating Stray Radiant Energy of Spectrophotometers", ANSI/ASTM E387-72.
Opler, A., Journal of the Optical Society of America, vol. 40, p. 401 (1950).
Stewart, J. E., (Infrared Spectroscopy, Experimental Methods and Techniques); Marcel Dekker, New York, 1970; pp. 231–251, 285, and 286.
Kaye, W., "Resolution and Stray Light in Near Infrared Spectroscopy", Applied Optics, vol. 14, No. 8, pp. 1977–1986 (Aug. 1975).

*Primary Examiner*—F. L. Evans
*Attorney, Agent, or Firm*—R. J. Steinmeyer; R. R. Meads; G. T. Hampson

[57] ABSTRACT

Methods for stray light measurement and compensation in spectrophotometers are disclosed. In one exemplary embodiment, stray light is determined as a convolution of a selected detected radiant power spectrum and a monochromator slit function. Such a stray light measurement may be made with or without the sample in an optical path between a source and detector within the spectrophotometer. When made with the sample in the optical path, the resulting stray light measurement may be used to compensate sample absorbance or transmittance measurements. In accordance with another embodiment of the present invention, sample absorbance or transmittance may be compensated in a method including measuring sample detected radiant power at a wavelength outside an interval of significant detected radiant power within which a sample measurement compensated for stray is desired.

13 Claims, 12 Drawing Figures

STRAY LIGHT MEASUREMENT AND COMPENSATION

BACKGROUND OF THE INVENTION

1. Field of the Invention

The present invention relates generally to the field of spectrophotometers and more particularly to the determination of stray light within such instruments and the compensation of sample measurements for stray light.

2. Description of the Prior Art

Spectrophotometers can be described as instruments that measure the relative amount of radiant energy absorbed or transmitted by a sample for one or more radiation wavelengths. Such instruments generally include a continuum radiation source, that is, one which generates radiant energy over a relatively broad band of wavelengths. A monochromator receives the radiation from the source and isolates an output beam comprising radiation having wavelengths substantially within a relatively narrow wavelength band.

The monochromator output beam is directed to a detector which produces an electrical output having a value related primarily to the radiant power received by the detector. Such detector output may be decreased by an amount equal to the detector output when radiation is blocked from the detector, generally called "dark current" or "dark signal". The resulting net output is called "detected radiant power" (DRP) and is the portion of the detector output generated only in response to incident radiant power.

The beam path between the monochromator and the detector is accessible to the user of the instrument so that sample or reference materials can be placed into the beam. Usually, the relative transmittance or absorbance of a sample with respect to a reference material is measured. For example, for given radiation wavelengths within the narrow wavelength band, the reference material is placed into the beam between the monochromator and the detector and the resulting DRP is measured. The reference material is removed and, with the sample in its place, a second DRP is measured. The sample transmittance is then expressed as a ratio of the second DRP with respect to the first DRP. Absorbance is related to transmittance by the conversion expression $A = -\log T$, where A is absorbance and T is transmittance. It will be recognized that although various examples and discussions included herein are presented in terms of transmittance, such examples and discussions are equally applicable to the measurement of absorbance since absorbance and transmittance are related terms for the same phenomenon.

The previously referred to monochromator wavelength band may be largely defined by two parameters, half bandwidth and central wavelength. The half bandwidth is generally identified as the difference between two wavelengths at which the DRP of the narrow wavelength band is one-half the maximum DRP in the band. The half bandwidth is usually determined by the width of monochromator entrance and exit slits through which the continuum radiation and the output beam pass, respectively. The interval or width of the narrow wavelength band is often considered to be twice the interval or width of the half bandwidth.

The central wavelength is the wavelength at the midpoint between the two wavelengths which define the half bandwidth. The central wavelength is adjusted by means of a mechanism that positions a prism or grating disperser within the monochromator. For manually adjusted spectrophotometers, the adjustment mechanism often includes a dial calibrated with respect to the central wavelength and the central wavelength is often referred to in the art as "monochromator dial setting" or simply "dial setting." More recently and particularly with microprocessor-based spectrophotometers, the adjustment mechanism is responsive and calibrated with respect to digital signals from the microprocessor with the digital signals controlling the central wavelength. Hence, where the term "dial setting" is used herein, it is to be understood as the central wavelength adjustment, regardless of the means thereof.

Ideally, the monochromator should pass only radiation having wavelengths within the narrow wavelength band, that is, the monochromator output beam should be free of radiation with wavelengths outside of an interval twice the width of the half bandwidth and centered at the central wavelength. However, such ideal monochromators do not exist. In addition to radiation with wavelengths within such an interval, which has been called "primary radiation," the monochromator output beam also includes radiation at wavelengths outside the interval of primary radiation. Such radiation has been referred to in the art as "stray light" and is often a result of light scattering within the monochromator.

While "stray light" is used herein as just described for the purpose of discussion of the prior art, it will be recognized by those skilled in the art that the term "stray light" has not been clearly defined or limited in use in the prior art. The term has been used variously to denote the overall problem of stray light in spectrophotometers, or a measured quantity of stray light, usually with unknown units, or dimensionless ratios such as stray light ratio and stray radiant energy. It will also be noted that light is synonymous with "radiation" and that "radiation" as used herein includes electromagnetic radiation throughout the ultraviolet, visible and infrared wavelength regions. The term "stray light" will be defined more precisely hereinbelow in the detailed description of the present invention.

Stray light is usually of interest in two contexts. First, it is a general practice of spectrophotometer instrument manufacturers to measure stray light for a particular spectrophotometer and to publish the measurement as an instrument performance specification. Periodically, a spectrophotometer should be retested to determine whether the spectrophotometer still meets the specification. A failure of the instrument to do so is an indication that the spectrophotometer performance may have degraded and that service may be required.

A second context is the measurement of sample transmittance where it is desirable to compensate for the effects of stray light. As described more fully hereinbelow, such compensation has not been heretofore possible to any significant degree of accuracy, and thus stray light has proven to be a source of uncertainty in transmittance measurements.

With respect first to the measurement of stray light as an indication of instrument performance, one accepted method of measuring stray light is set forth in the "Standard Method of Estimating Stray Radiant Energy" published by the American Society for Testing Materials (ASTM) (ANSI/ASTM E387-72 Reapproved 1977). The ASTM method defines the resulting measurement as stray radiant energy (SRE).

Briefly, such a method involves the measurement of the transmittance of a test material at a wavelength where the material is known to be essentially opaque. The observed transmittance is considered to arise solely from stray light and is directly equal to SRE.

As an example of the ASTM method, one accepted test material for use therewith is a one centimeter path length aqueous solution containing 50 g/L of $NaNO_2$. Such a test solution exhibits a relatively sharp transmittance cutoff at about 400 nm and is essentially opaque in a range of wavelengths from 300 nm to 385 nm (reaching an A of about 16.8 at 355 nm). With the monochromator dial setting adjusted to a wavelength within the 300–385 nm range, the transmittance of the test solution is measured.

For example, with the dial setting at 355 nm and assuming the monochromator half bandwidth to be 2 nm, then primary radiation is radiation having wavelengths between 353 nm and 357 nm. Such primary radiation interval is relatively narrow as compared to the 300–385 nm absorption range of the test solution. Thus, the test solution is highly absorbing throughout the primary radiation interval and essentially absorbs all of the radiation therein. If the monochromator were perfect and the output beam included only primary radiation, essentially no radiation would be transmitted by the test sample and thus no radiant power would be detected by the detector.

However, the monochromator output beam also includes stray light having wavelengths outside the interval of primary radiation. More importantly, a portion of the stray light has wavelengths which are not absorbed by the test solution and therefore pass through the test solution to the detector. Thus, even though the monochromator dial setting is in a wavelength region where the test solution absorbs in essence all of the primary radiation, stray light still reaches the detector. The amount of the detected stray radiant power divided by the total detected radiant power when the test material is not in the beam is called the SRE and gives some indication of instrument performance.

The ASTM method of measuring SRE is deficient in several respects. First, the method can only be performed at wavelengths defined by the spectral characteristics of known and accepted test materials. Such wavelengths may not fully cover the wavelength range of an instrument to be tested. Consequently, instrument performance specifications for stray light using the ASTM method are often given for only one wavelength within the instrument wavelength range, an inadequate indication of instrument performance.

Another important drawback of the ASTM method is that the test material always absorbs at least some of the stray light. In the example described above, the $NaNO_2$ solution absorbs essentially all radiation within a 300–385 nm range. The extent to which the test material absorbs stray light introduces an error into the measurement of SRE.

Also, the ASTM method of determining SRE is not an accurate measure of stray light as previously defined, which is light having wavelengths outside the interval of primary radiation. In order to perform such an experimental measurement using the ASTM method, it would be necessary to use a test material that is essentially opaque only over the relatively narrow primary radiation interval. Such a test material does not exist.

In an effort to overcome the limitations of the ASTM SRE measurement method, Dr. Kaye, the inventor named herein, developed a stray light measurement technique for determining instrument performance. Dr. Kaye's technique did not require a test material as used in the ASTM method and thus overcame the difficulties associated with test material selection and use. In addition, Dr. Kaye's measurement technique could be automated in a spectrophotometer to provide the user with an indication of current instrument stray light performance for comparison to the original instrument stray light specification. Such automation has been implemented in the model DU ®-5 and model 42 instruments manufactured by Beckman Instruments, Inc., the assignee of the present invention.

In order to present an example of the measurement technique, it is to be noted that the DU-5 and model 42 instruments internally define a plurality of fixed wavelength intervals which limit detector response to radiation with wavelengths within the respective interval. For each monochromator dial setting within the instrument wavelength operating range, one of the fixed wavelength intervals is selected such that the selected fixed wavelength interval includes the monochromator dial setting. The fixed wavelength intervals are defined by the spectral sensitivity characteristics of the source radiation, by the spectral sensitivity characteristics of the detector, by blocking filters or combinations thereof. For example, a fixed wavelength interval can be defined by a bandpass blocking filter placed in the monochromator output beam. Such a blocking filter passes radiation within the fixed wavelength interval but is essentially opaque to radiation with wavelengths outside the fixed wavelength interval. Consequently, radiation with wavelengths outside the fixed wavelength interval is blocked from the detector, thus limiting detector response to radiation with wavelengths within the fixed wavelength interval.

In the DU-5 and model 42 instruments, the operator first selects the stray light test. The instrument then responds with visual instructions to select a test wavelength, $\lambda_1$, to remove any sample from the beam and to place a reference material or blank into the beam. Once the operator follows the instructions, the operator commands the instrument to automatically continue the performance measurement. In doing so, the monochromator dial setting is adjusted to the test wavelength $\lambda_1$ and the proper fixed wavelength interval including $\lambda_1$ is selected. Such selected fixed wavelength interval may be defined by a bandpass blocking filter as previously described. A first detected radiant power ($DRP_1$) measurement is then made. It is to be noted that with the dial setting adjusted to $\lambda_1$, the DRP is in response to both primary and stray radiation in the monochromator output beam having wavelengths within the selected fixed wavelength interval.

Once $DRP_1$ at $\lambda_1$ is determined, the monochromator dial setting is adjusted to a second wavelength $\lambda_2$ outside the selected fixed wavelength interval in which $DRP_1$ was measured. However, the bandpass blocking filter and thus the selected fixed wavelength interval are not changed. Thus, the instrument continues to operate as though the monochromator dial setting is within the selected fixed wavelength interval first selected for $\lambda_1$. With the monochromator dial setting thus adjusted, a second DRP, $DRP_2$, is measured. Because $\lambda_2$ is outside the selected fixed wavelength interval, primary radiation in the monochromator output beam does not effectively contribute to $DRP_2$. However, the monochromator output beam also includes stray light as previously described. Such stray light having wavelengths within the selected fixed wavelength interval continues to fall on the detector. Hence, $DRP_2$ is essentially in response to only the stray light within the selected fixed wavelength interval. To find the relative intensity of the stray light at $\lambda_1$, the ratio $DRP_2/DRP_1$ is calculated similar to transmittance and is expressed as a percentage.

Although the technique just described is a substantial improvement over the ASTM standard method because it does not require a separate test material, the resulting instrument performance measurement is based on the assumption that the stray light measured with the dial setting adjusted to $\lambda_2$ is equal to the stray light present with the dial setting adjusted to $\lambda_1$. It should be noted that a similar assumption is inherent in the ASTM SRE measurement in that the SRE is assumed to remain constant in the vicinity of the absorption edge of the test material. Such an assumption results in providing an approximation of instrument stray light performance at $\lambda_1$. Where a more precise measure of stray light is required, such a technique as just described may not provide the needed precision. Thus, there exists a need for an instrument performance stray light measurement method that provides more accurate results.

As noted previously, a second context in which stray light is of interest is in the measurement of sample transmittance (or absorbance). Particularly, stray light can be of interest where a transmittance measurement is made of a sample having a relatively low transmittance (e.g. about $10^{-2}$ or lower) and where the sample transmittance is not constant at all wavelengths.

An example of this can be seen with reference to the above discussion of the ASTM SRE method. The $NaNO_2$ test solution essentially blocks all radiation having a wavelength of 355 nm. However, the solution does pass radiation having other wavelengths, notably at wavelengths greater than 420 nm. If one were to attempt to measure the transmittance of the test solution of $NaNO_2$ at, for example, 355 nm, the test solution would absorb essentially all of the light in the monochromator narrow wavelength band centered at 355 nm, that is, essentially all of the primary radiation. However, stray light in the monochromator output beam with wavelengths greater than about 420 nm is transmitted by the solution to the detector, giving rise to a detector output. Because the absorbance of the test solution at 355 nm is approximately 16.8, the resulting transmittance measurement based on the detector output results essentially entirely from stray light passing through the solution at wavelengths where the solution is not highly absorbing. If such a transmittance measurement were not corrected or compensated for stray light, the error inherent therein could have a serious impact on the conclusions drawn from the spectroscopic analysis of the test solution.

In an effort to reduce the influence of stray light on sample measurements, it is known in the art to employ two monochromators in the instrument. Such double monochromator instruments, however, are costly and the two monochromators significantly reduce the intensity of the beam.

It has also been known to attempt to correct transmission data for the effects of stray light. For example, A. Opler in the *Journal of the Optical Society of America*, Volume 40, page 401 (1950), presented tabulated correction factors for the errors expected from unabsorbed stray light. However, Opler, as well as others, have heretofore failed to accurately account for the influence that the sample will have on stray light. Unless the fraction of stray light absorbed by the sample is known or can be determined, transmission correction is merely speculative and may well under or over correct the transmittance measurement. Moreover, the sign of an error attributable to stray light (i.e., whether the sample transmittance value should be increased or decreased) depends upon whether the sample or the reference absorbs more of the radiation within the monochromator narrow wavelength band or the stray light radiation. Thus, it is possible to increase an error due to stray light if the attempted correction or compensation amount is of the wrong sign.

Heretofore, no method existed for accurately correcting a sample transmittance value for stray light. The ASTM method for the measurement of SRE provides an SRE only for an instrument in the presence of the test material. While such an SRE may be useful in establishing comparisons of SRE between instruments, the SRE provides no accurate predictive value as to the influence that stray light will have on the measured transmittance of other samples. Moreover, because SRE depends upon the presence of the test material in the beam, sample transmittance could not be measured at all in the wavelength region where the test material is essentially opaque. Also, in instruments which define a plurality of fixed wavelength intervals as previously described, the SRE becomes less accurate for a fixed wavelength interval as the interval becomes narrower. Such a result occurs because the stray light within the fixed wavelength interval may be almost completely absorbed by the test material.

The instrument performance measurement technique described above and as used in the model DU-5 and model 42 instruments, provides a more accurate instrument specification. However, even if a sample were inadvertently left in the beam for the automatic measurement performance measurement despite the operator instructions to the contrary, the resulting ratio would be meaningless and of no use in a stray light compensation context.

Thus, there is a need for a method for compensating transmittance and absorbance measurements for stray light.

SUMMARY OF THE INVENTION

The methods in accordance with the present invention overcome the limitations set forth above and meet the needs of stray light compensation and an improved instrument performance test for stray light.

In accordance with one embodiment of the present invention and as is described more fully hereinbelow, stray light is defined as detected radiant power of wavelengths more than L units away from the central wavelength, $\overline{\lambda}$, of the monochromator narrow wavelength band. Stray light is determined by a convolution (an integration of the product of two or more functions) of a monochromator slit function with a selected DRP spectrum. Briefly, the monochromator slit function can be described as a plot of monochromator output as a function of dial setting when monochromatic radiation illuminates the monochromator entrance slit. The selected DRP spectrum is determined at least over an interval of significant DRP which may be defined by source spectral emission, detector spectral sensitivity, and transmission of all optics in an optical path between the source and the detector. In practice, the selected DRP spectrum may be largely determined by a blocking filter, except at either end of the overall instrument wavelength operating range. The selected DRP spectrum includes the wavelength at which the stray light is to be determined. For a measure of instrument performance, the selected DRP spectrum is determined with no sample in the optical path. The convolution is approximated by a summation of the products of the monochromator slit function and the selected DRP spectrum through a range of wavelengths which exclude an interval defined by ±L (interval of primary radiation). The selected DRP spectrum can alternatively and advantageously be measured with a sample in the optical path and the resulting convolution in accordance with the present invention provides a measure of stray light in the presence of the sample. Further in accordance with the present invention, a difference between a sample DRP at the stray light measurement wavelength and the measured stray light provides sample DRP compensated or corrected for stray light. A ratio of the difference to a reference DRP at the stray light measurement wavelength uniquely provides sample transmittance compensated for stray light.

In yet another embodiment of the present invention, sample measurements can be easily compensated for stray light without performing the convolution described above. In such an embodiment, a reference DRP measurement is taken at $\overline{\lambda_1}$ and a sample DRP measurement is also made at $\overline{\lambda_1}$. The wavelength $\lambda_1$ is within an interval of significant DRP. It is to be noted that the ratio of the sample DRP to the reference DRP so measured provides a conventional measure of sample transmittance but not compensated for stray light. To enable stray light compensation, a third DRP measurement is made with the sample in the beam at a monochromator dial setting $\overline{\lambda_2}$ outside the interval of significant DRP within which $\overline{\lambda_1}$ lies. The ratio of the difference between the sample DRP at $\overline{\lambda_1}$ and $\overline{\lambda_2}$ to the reference DRP at $\overline{\lambda_1}$ easily and simply provides sample transmittance corrected for stray light.

Stray light measurement and compensation as performed by the present invention effectively increases the accuracy and range of spectrophotometers through unique and inventive techniques heretofore not available in the field of spectroscopy.

DETAILED DESCRIPTION

Turning now to a detailed description of the invention, a definition of stray light in accordance with the present invention will first be described to aid in the understanding of the invention. A general description of the present stray light measurement method will then be set forth, followed by a detailed description of a preferred method. Lastly, stray light compensation in accordance with the present invention is described in detail.

First as to a more precise definition of stray light, stray light is defined in accordance with the present measurement method as the detected radiant power (DRP) of light having wavelengths more than a limit L wavelength units away (that is, ±L) from the central wavelength, $\overline{\lambda}$, of the monochromator narrow wavelength band. Thus, to specify a stray light measurement, the wavelength $\overline{\lambda}$ and the limit L must be specified. The stray light so specified is represented herein as $S(\overline{\lambda}, L)$.

A measure of stray light is often of little practical use because, among other reasons, the units in which stray light is measured are difficult to define. Of more interest is a ratio between the measured stray light and a reference DRP at the stray light measurement wavelength. Such a ratio eliminates the necessity of defining stray light units and is referred to hereinafter as a stray light ratio (SLR).

Figure 1:
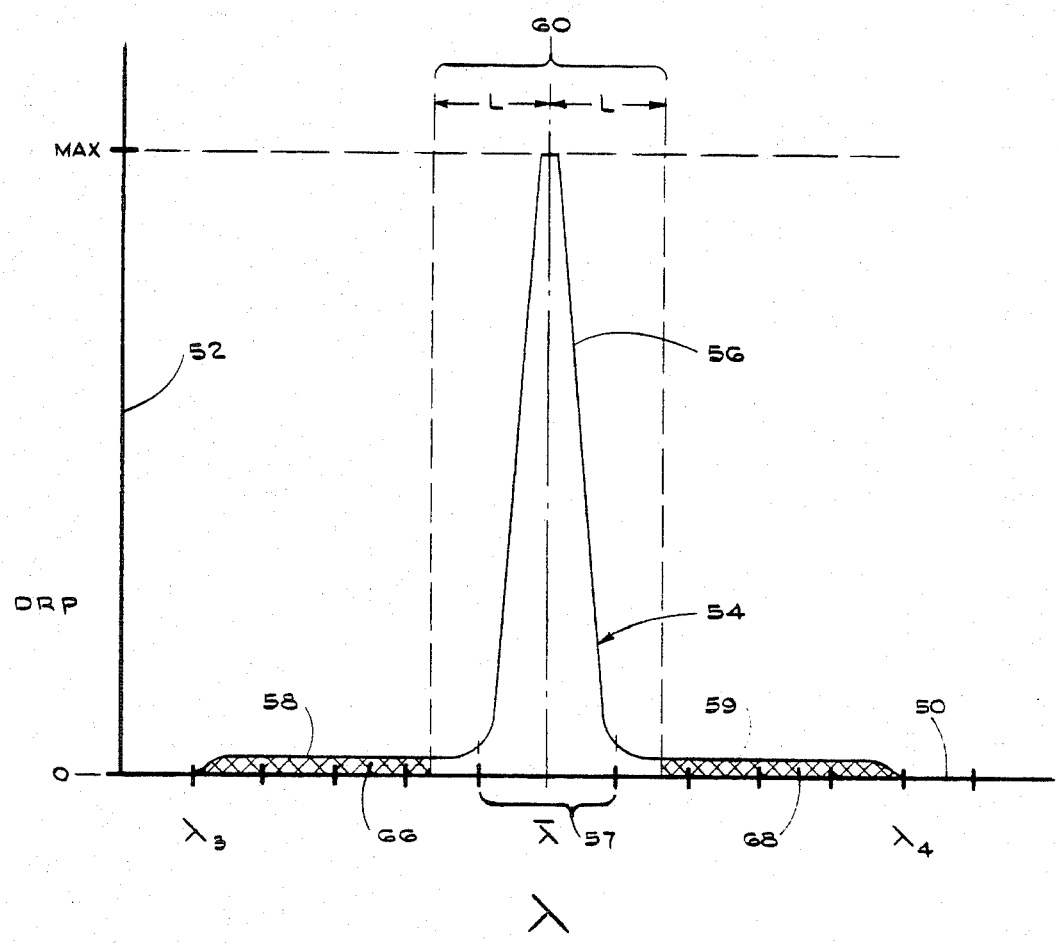
FIG. 1 is a simplified curve describing the spectral character of radiation detected in a spectrophotometer and is useful for illustrating a definition of stray light in accordance with the present invention.
Figure 1A:
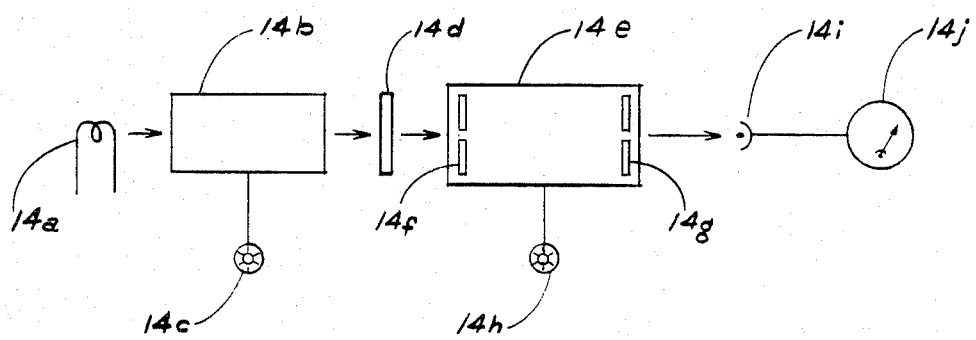
FIG. 1A is a schematic diagram of an experimental spectrophotometer useful for illustrating the stray light definition with FIG. 1.

The definition of stray light specified by $S(L, \overline{\lambda})$ may be further illustrated with reference to FIGS. 1 and 1A. FIG. 1 is a DRP spectrum 54 for a hypothetical experimental spectrophotometer as seen in FIG. 1A. An abscissa 50 of FIG. 1 represents wavelength and an ordinate 52 thereof represents DRP.

In FIG. 1A, a continuum source of radiation 14a generates continuum radiation that is applied to an ideal or perfect monochromator 14b. The perfect monochromator 14b generates an output beam with a central wavelength controlled by a dial 14c. The output beam is directed through a bandpass blocking filter 14d to a monochromator under test, 14e. The test monochromator 14e includes conventional entrance and exit slits, 14f and 14g, respectively, and a control or dial 14h which controls the central wavelength of the output beam isolated by the monochromator 14e. The test monochromator 14e output beam is directed to a detector 14i that generates a DRP indicated by suitable indicating means 14j. For the present example, it is assumed that the perfect monochromator 14b has a considerably narrower half bandwidth than the test monochromator 14e, that the perfect monochromator 14b passes only primary radiation, and that monochromatic radiation can pass unobstructed therethrough.

With such an experimental spectrophotometer, assume that the test monochromator dial 14h is adjusted to some wavelength $\overline{\lambda}$ within the fixed wavelength interval defined by the blocking filter 14d. The DRP spectrum 54 of FIG. 1 is obtained by plotting the DRP indicated by the means 14j as a function of wavelength λ determined by the dial 14c. At the test monochromator dial setting $\overline{\lambda}$, a maximum (MAX) DRP is indicated by means 14j. The MAX DRP is a function of source intensity, transmittance of the blocking filter 14d, the transmission properties of the test monochromator 14e (determined largely by the slits 14f and 14g) and the sensitivity of the detector 14i.

The spectrum 54 is typical of monochromator DRP spectra and includes a generally triangular portion 56. The half bandwidth of the monochromator (also sometimes referred to as monochromator resolution) is determined primarily by the width of the slits 14f and 14g. Most of the detected radiation is seen to fall within a half bandwidth of the central wavelength, that is, within an interval 57 centered at $\overline{\lambda}$.

Although most of the detected radiation is within a half bandwidth of the central wavelength, a small DRP is still detectable at wavelengths considerably further than one-half bandwidth away from $\overline{\lambda}$. Such signals are indicated at 58 and 59 in FIG. 1. At wavelength $\lambda_3$ and $\lambda_4$, the DRP drops essentially to zero. The wavelengths $\lambda_3$ and $\lambda_4$ are determined primarily by the pass band of the blocking filter 14d and, to a lesser extent, by the spectral content of the source 14a radiation and the detector 14i sensitivity.

A wavelength interval 60 is defined on either side of the dial setting wavelength $\overline{\lambda}$ by the limit L. Radiation with wavelengths between $\overline{\lambda} \pm L$ indicated by the interval 60 is defined as primary radiation and radiation with all other wavelengths is defined as stray light. In FIG. 1, the stray light $S(\overline{\lambda}, L)$ comprises cross hatched portions 66 and 68 between the spectrum 54 and the abscissa 50. The choice of L is dependent upon experimental needs and limitations, as is described more fully hereinbelow. However, L cannot be less than the half bandwidth, that is, one-half the interval 57. The stray light ratio (SLR) is equal to a ratio of the area comprising the cross hatched portions 66 and 68 to the total area under the curve 54.

As will be understood by those skilled in the art, FIG. 1 is used here for purposes of illustration only and the spectrum 54 is not intended to accurately depict the spectral content in the output beam of any specific monochromator. The spectrum 54 is of necessity smoothed and simplified. Also, portions of the spectrum 54 are expanded and the DRP scale is not necessarily uniformly linear or logarithmic. For example, the stray light intensities within the regions 66 and 68 may be approximately one thousand to one million or more times less intense than the maximum DRP MAX. However, FIG. 1 is useful to illustrate the terms "stray light" and "stray light ratio" in the Detailed Description.

Generally, the stray light determination method in accordance with the present invention is capable of measuring stray light as an indication of instrument performance or stray light in the presence of a sample. In either instance, the method requires that the monochromator slit function and a selected DRP spectrum first be determined.

The monochromator slit function can be described as a plot of monochromator output as a function of dial setting when monochromatic radiation is applied to the monochromator entrance slit.

The selected DRP spectrum is a DRP spectrum measured as a function of dial setting at least over an interval of significant DRP (sometimes referred to hereinafter as ISD). Such an ISD may be defined by a blocking filter as is described more fully hereinbelow. Where a measure of instrument performance is desired, the selected DRP spectrum is determined over the ISD with no sample in the monochromator output beam. However, where stray light is to be determined in the presence of a sample, the selected DRP spectrum is measured over an ISD with the sample in the monochromator output beam.

With both the monochromator slit function and the selected DRP spectrum available, stray light is then determined in accordance with a convolution approximated by the following summation:

$$S(\overline{\lambda}, L) = K \left( \sum_{n=-\infty}^{-L/\Delta} P(\overline{\lambda} - n\Delta)F(n\Delta) + \sum_{n=L/\Delta}^{\infty} P(\overline{\lambda} - n\Delta)F(n\Delta) \right) \quad \text{(Eq. 1)}$$

where
$P(\overline{\lambda} - n\Delta)$ is a selected DRP spectrum;
$F(n\Delta)$ is a monochromator slit function;
K is a proportionality constant;
$\overline{\lambda}$ is monochromator dial setting at which the stray light is determined;
L is a predetermined limit distinguishing primary radiation from stray light;
$\Delta$ is a finite wavelength increment; and
n is an iterating integer.

The range of values for the iterating integer n, must be determined such that $P(\overline{\lambda} - n\Delta)$ extends over an interval of significant DRP. The values of n are found in accordance with $$n\Delta = \lambda - \overline{\lambda} \quad \text{(Eq. 2)}$$

where $\lambda$ is wavelength over the interval of significant DRP. The summation is not performed at wavelengths within a range defined by the limit L, that is, the range of primary radiation.

The proportionality constant K may be determined experimentally by performing the convolution for a monochromator dial setting outside the interval of significant DRP and selecting K such that the calculated stray light is equal to measured DRP at such dial setting. Then, stray light calculations for the selected DRP spectrum within the interval of significant DRP can be made using the proportionality constant K. A stray light ratio (SLR) at a dial setting $\overline{\lambda}$ may be determined as the ratio of the stray light at the dial setting $\overline{\lambda}$ determined in accordance with the present invention to the DRP at the monochromator dial setting $\overline{\lambda}$.

It will be apparent to those skilled in the art that as $\Delta$ approaches an infintesimally small increment, the convolution of Equation (1) can be expressed as an integral. If the selected DRP spectrum and the slit function can be expressed mathematically as functions, then such an integral may be solved to determine stray light in accordance herewith. Such an integral is discussed in an article entitled "Stray Light Ratio Measurements" in the December, 1981 issue of *Analytical Chemistry*, Vol. 53, No. 14, pp. 2201-2206. However, it is usually not possible to find such mathematical expressions and thus a summation as in Equation (1) is instead used.

Exemplary methods for determining the monochromator slit function and the selected DRP spectrum will now be discussed.

With respect first to the monochromator slit function, such a function can be described as a plot of monochromator output as a function of the monochromator dial setting when substantially monochromatic light is applied to the monochromator. Generally, to obtain such a slit function when monochromatic radiation is applied to the monochromator, the dial setting is varied over wavelengths extending below and above the monochromatic light wavelength. The detected radiant power (DRP) of the monochromator output beam is detected by a suitable detector. The slit function is then usually expressed as a plot of DRP versus the difference between the dial setting and the monochromatic light wavelength. In order to accommodate the large dynamic range of the DRP values, it is customary to plot the DRP on a logarithmic scale.

A slit function for a monochromator under test may be conveniently determined with a spectrophotometer within which the monochromator is used. It will be recognized by those skilled in the art that the spectrophotometer used for such slit function determination must have a good signal-to-noise ratio and that means must be available for amplifying the detector output signal by relatively large factors. Such instruments and means are well known to those skilled in the art.

Figure 2:
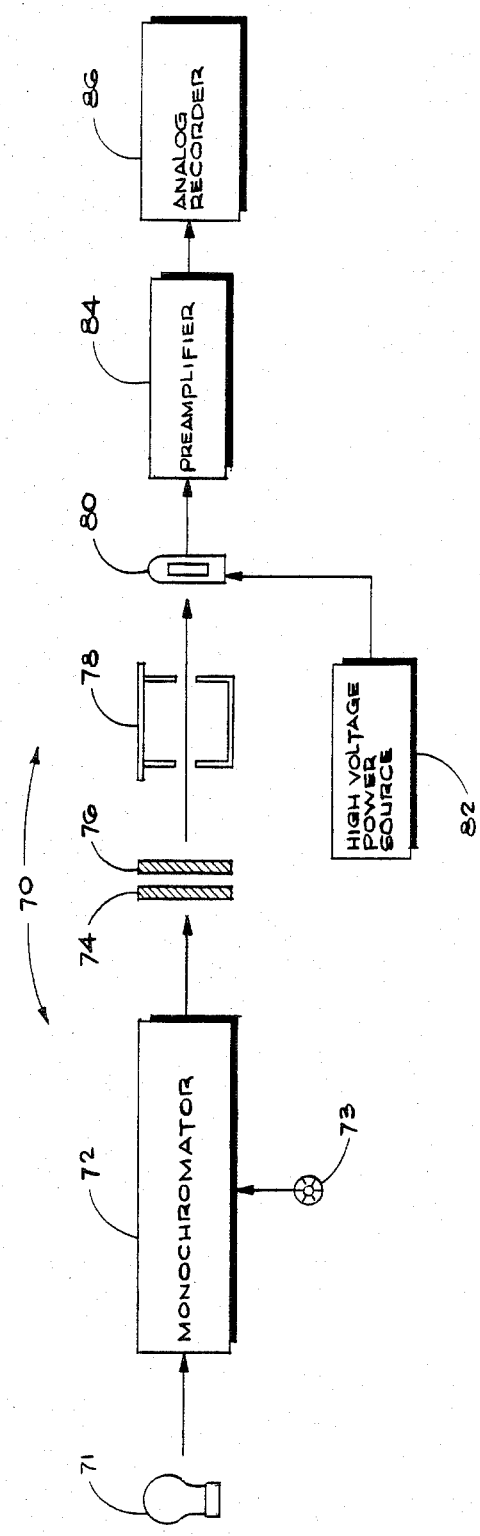
FIG. 2 is a simplified block diagram of a spectrophotometer modified to provide a measure of monochromator slit function.

A spectrophotometer 70 for determining a slit function is seen in simplified schematic form in FIG. 2. the spectrophotometer 70 includes a low-pressure mercury-vapor lamp 71 which is a line source of monochromatic radiation. Such radiation has a wavelength $\lambda$ and is applied to a monochromator 72 to be tested. The central wavelength of the monochromator 72 narrow wavelength band is adjusted by means of a control 73 calibrated with respect to the central wavelength. The central wavelength is referred to as the monochromator dial setting, $\bar{\lambda}$.

Figure 3:
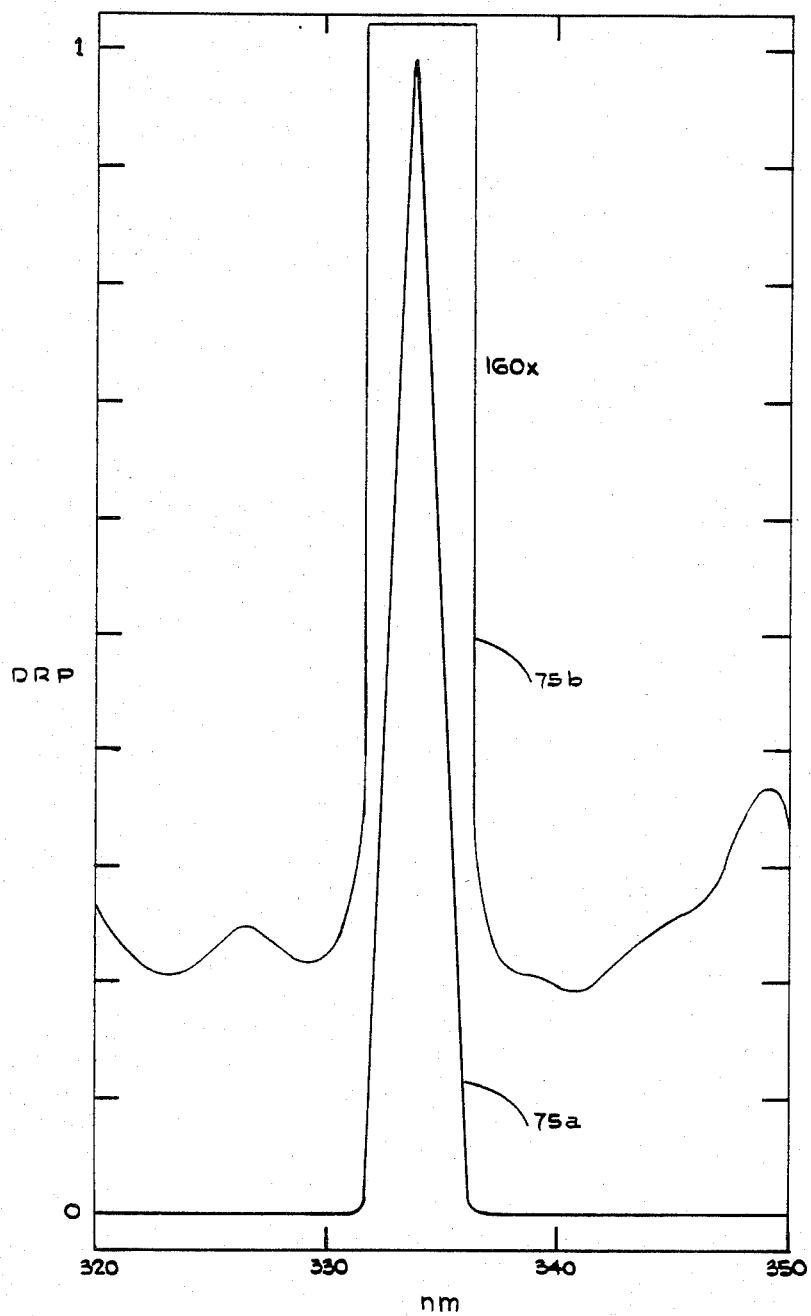
FIG. 3 is an emission spectrum of the lamp of FIG. 2.

Although the lamp 71 generates monochromatic radiation, the lamp 71 also emits some continuum radiation. For example, FIG. 3 shows an emission spectrum 75a for the lamp 71 in the vicinity of 334 nm. The majority of the radiation is of 334 nm. However, the spectrophotometer has a finite resolution which converts the spectral line at 334 nm into a triangular band shown by the spectrum 75a. The half bandwidth of the triangular band is equal to the resolution of the monochromator 72.

The continuum radiation emitted by the lamp 71 is seen only when expanding the ordinate of FIG. 3. A curve 75b depicts the emission spectrum 75a of the lamp 71 expanded 160 times. With such a scale expansion, the continuum radiation is seen on either side of the triangular portion of spectrum 75a.

Such continuum radiation may be reduced to insignificance by means of suitable filters. In the exemplary embodiment disclosed herein, two isolating filters 74 and 76 are disposed in the monochromator 72 output beam. The filters 74 and 76 are high-quality narrow band interference filters. The filters are three-cavity Ditric interference filters used to isolate the 334 nm spectral singlet line of the lamp 71.

Figure 4:
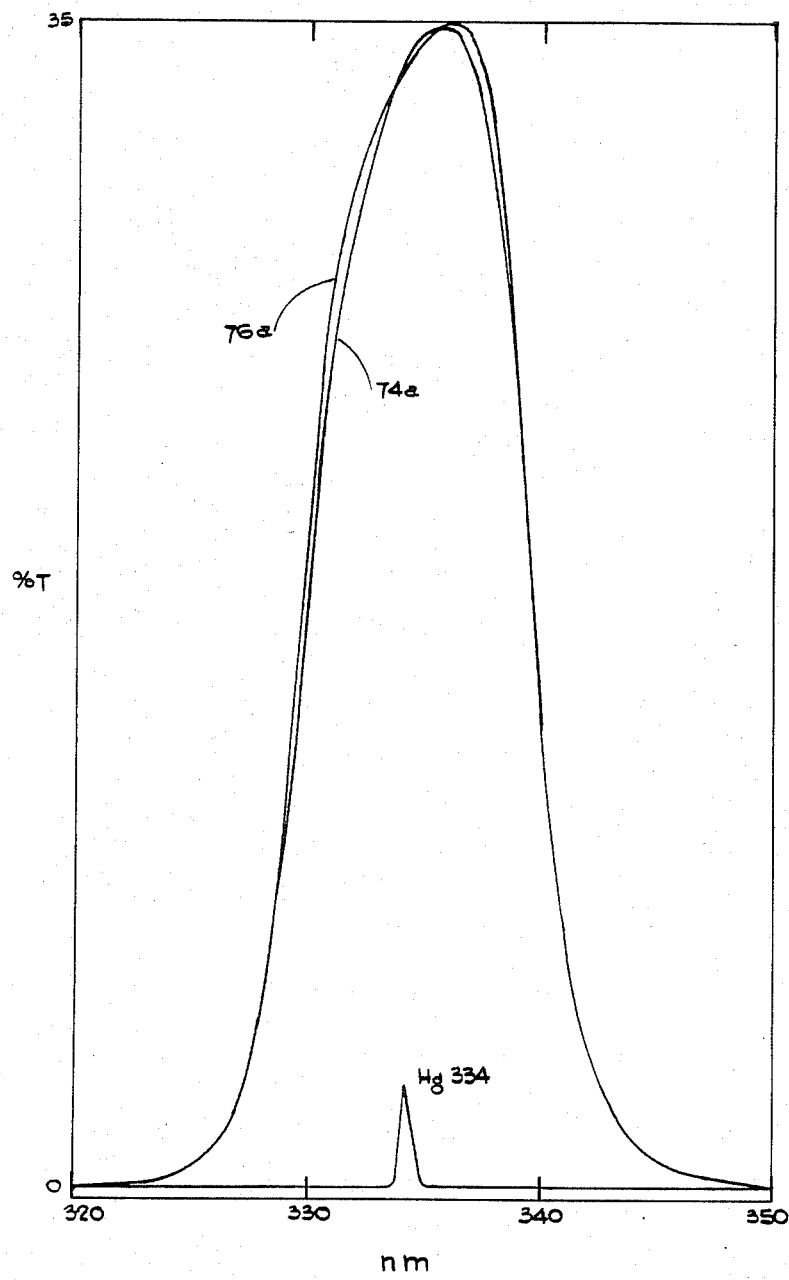
FIG. 4 depicts normalized transmittance spectra for the isolation filters of FIG 2.

Transmittance spectra for the filters 74 and 76 are seen in FIG. 4. Such transmittance spectra are measured using a suitable spectrophotometer such as a Model 5270 Spectrophotometer manufactured by Beckman Instruments, Inc., the assignee of the present invention. Other suitable spectrophotometers are well known to those skilled in the art.

In FIG. 4, a first curve 74a illustrates the transmittance spectra for the filter 74 while a second curve 76a illustrates the transmittance spectra for the filter 76. From FIG. 4, it is seen that the transmittance of each filter falls to approximately $10^{-3}$ at 323 and 347 nm. It may then be calculated that the transmittance of the two filters in series is $10^{-6}$ at such wavelengths. When both filters are placed in series with the line source as seen in FIG. 2, the continuum radiation at $\bar{\lambda}=323$ and 347 nm will be approximately 0.0001% of the radiation at 334 nm. Moreover, at wavelengths further removed from 334 nm, the radiation is of still lower intensity. Any DRP larger than such value at dial settings $\bar{\lambda}$ less than 323 or greater than 347 must be indicative of the transmission of 334 nm radiation rather than the transmission of continuum radiation at the dial setting $\bar{\lambda}$. In practice, the DRP from the 334 nm radiation is far greater than that from the continuum radiation when $|\bar{\lambda}-\lambda|>15$ nm such that a recorded spectrum is a valid representation of the slit function outside such an interval.

The radiation from the filters 74 and 76 passes through a sample compartment 78 and in turn to a detector 80. The detector 80 dynode voltage is provided by a high voltage power surface 82. Such a high voltage power source can be the power supply within the spectrophotometer 70 under test or may be an external regulated power supply such as a Hewlett-Packard Model 5621A. The output of the detector 80 is applied to a preamplifier 84, the output of which is in turn recorded by an analog recorder 86. Thus, an optical path is defined between the lamp 72 and the detector 80, with the monochromator 72, filters 74, 76 and sample compartment 78 in the optical path.

It is to be recognized that the spectrophotometer 70 of FIG. 2 is a modified instrument of otherwise conventional design. For example, such an instrument can be a model DU®-8 spectrophotometer manufactured and sold by the assignee of the present invention. The spectrophotometer 70 is modified generally by using the low-pressure mercury-vapor lamp 71, insertion of the isolation filters 74 and 76, and, if necessary, the use of an external high voltage power supply. If the spectrophotometer 70 uses blocking filters as described previously, such blocking filters are removed or disabled when determining the monochromator slit function.

The slit function for the spectrophotometer 70 of FIG. 2 is recorded by varying the monochromator dial setting (via the control 73) from the monochromatic source wavelength (334 nm herein) and recording the preamplifier 84 output. The preamplifier 84 output is compensated for detector dark current, which is to say that the resulting output is DRP. For the embodiment of FIG. 2, the slit function is as shown by curves 88a in FIG. 5. The ordinate is log DRP with respect to the difference between dial setting, $\lambda$, and monochromatic source wavelength, $\lambda$, on the abscissa. As discussed previously, the slit function of FIG. 3 is valid in all wavelengths outside of the interval $|\bar{\lambda}=\lambda|>15$ nm.

Figure 5:
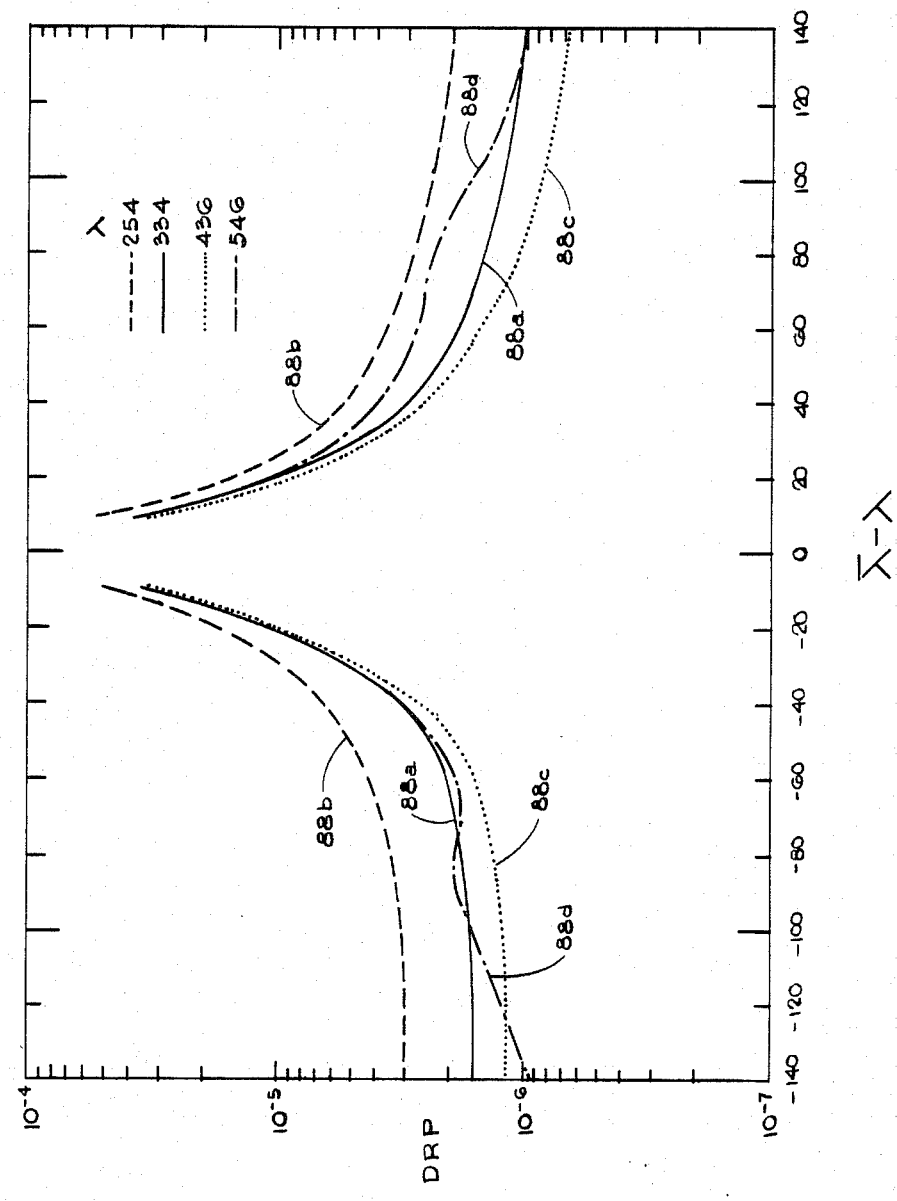
FIG. 5 depicts slit functions of the monochromator of FIG. 2 at several monochromatic radiation wavelengths.

As will be understood by those skilled in the art, the logarithmic representation of DRP in FIG. 5 represents a substantial DRP dynamic range. Any suitable means for detecting such DRP may be employed as will be apparent to those skilled in the art. In the embodiment disclosed herein, the scale expansions used for detecting DRP were generated by, for example, varying the gain of the preamplifier 84, the attenuation at the input of the analog recorder 86, and by varying the detector 80 dynode voltage as provided by the high voltage power source 82 to thereby vary the detector 80 sensitivity.

Those skilled in the art will recognize other suitable methods of generating monochromatic light for the purpose of measuring a slit function. For example, instead of using a line source filtered through interference filters, a continuum source may be used filtered through appropriate narrow band filters. In such an instance and where the slit function and the selected DRP spectrum are both normalized, the constant K of Equation (1) will be equal to $\Delta$. Still other methods of generating monochromatic light include utilizing radiation from a laser or employing a second monochromator to isolate a narrow band of radiation from either a continuum or line source.

With the monochromator slit function known, the selected DRP spectrum must be determined before the convolution is performed. Generally, the selected DRP spectrum is obtained by plotting a dark-current compensated detector output as a function of monochromator dial setting $\bar{\lambda}$ when radiation from a continuum source is applied to the monochromator. For a measure of instrument stray light performance, the selected spectrum determination is made with no sample in the beam and over at least an interval of significant DRP within which the stray light determination is to be made.

To obtain such a DRP spectrum, the source 71 is replaced with a source ordinarily used in the instrument. For example, a tungsten-halogen lamp 90 (FIG. 6) is the continuum light source generally used in a spectrophotometer 70 for light within the visible and near ultraviolet range while a deuterium lamp may be used at wavelengths shorter than about 315 nm.

Figure 6:
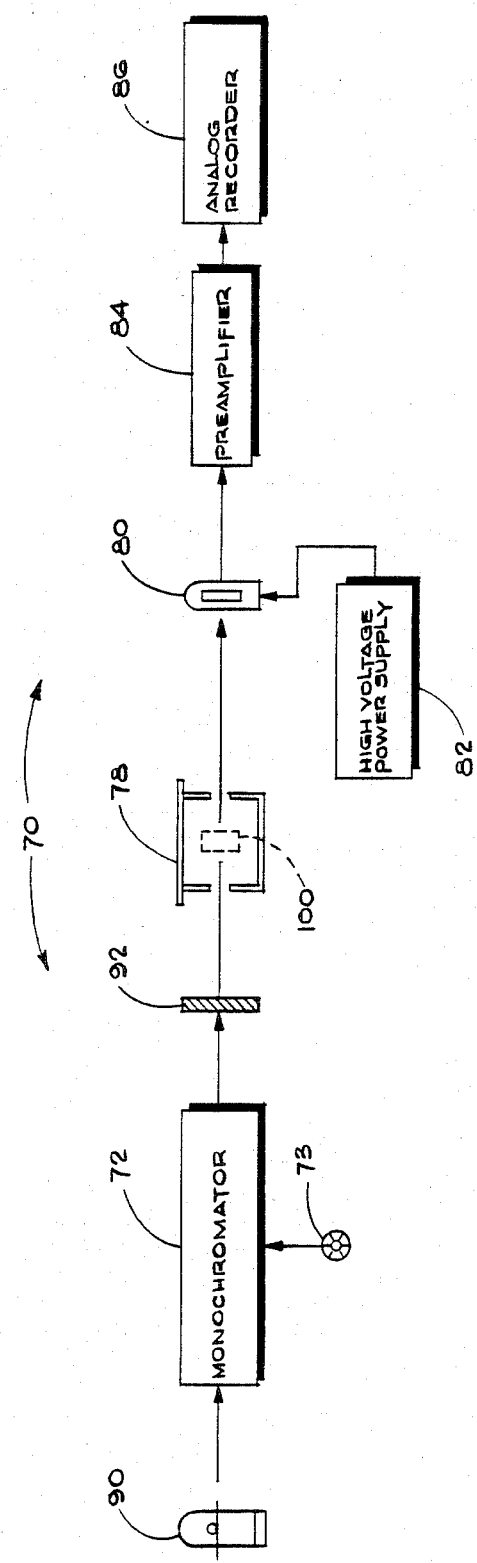
FIG. 6 is a simplified block diagram of a spectrophotometer which may be used in performing the method of the present invention.

The filters 74 and 76 of FIG. 2 are replaced in FIG. 6 with a bandpass blocking filter 92. The blocking filter 92 defines an interval of significant DRP.

Figure 7:
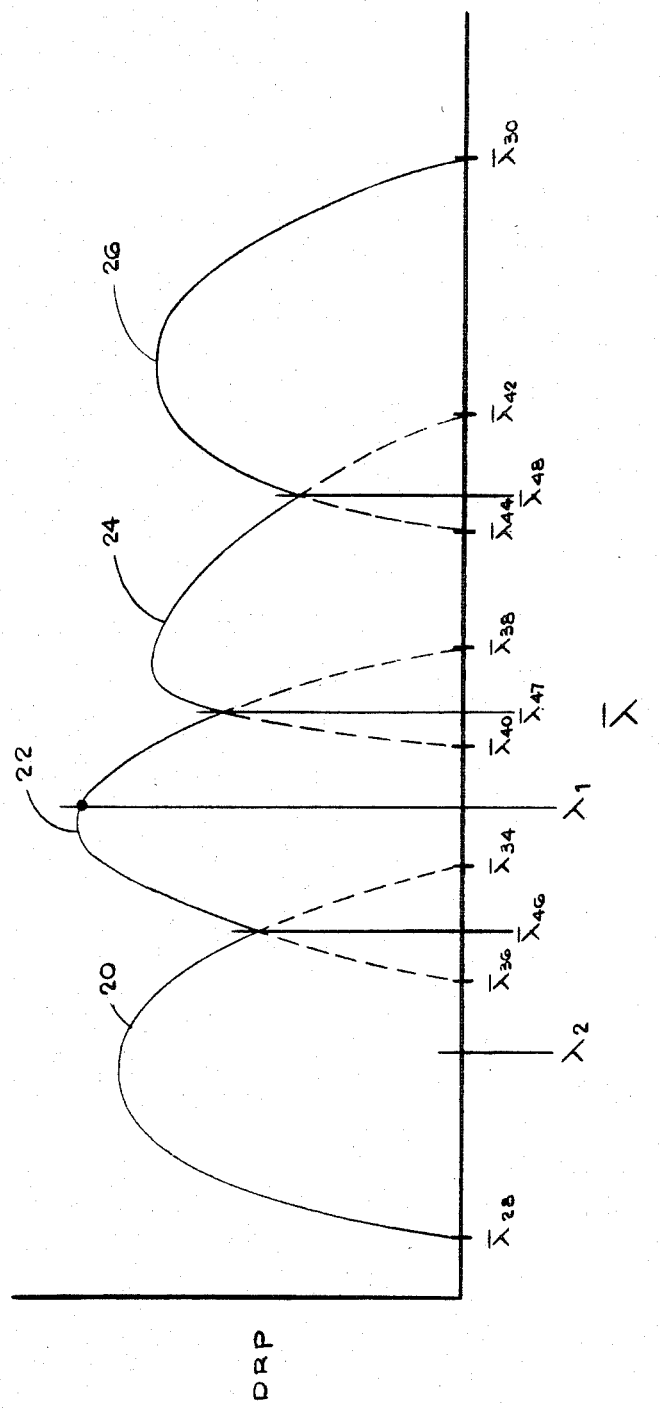
FIG. 7 depicts intervals of significant detected radiant power.

An interval of significant DRP (ISD) as used herein is better understood with reference to FIG. 7. FIG. 7 illustrates a plurality of instrument DRP curves plotted on a linear scale with respect to dial setting, $\bar{\lambda}$. The term instrument DRP is used here to indicate that the DRP is not influenced by any sample or reference material in the monochromator output beam. Four instrument DRP curves 20, 22, 24 and 26 overlap to define an instrument operating range shown by the solid line from $\bar{\lambda}_{28}$ to $\bar{\lambda}_{30}$. It is seen that each of the instrument DRP curves defines a respective interval of significant DRP outside of which essentially no DRP exists. Such intervals were referred to hereinbefore as fixed wavelength intervals. For example, the DRP curve 20 defines an interval of significant DRP (ISD) from $\bar{\lambda}_{28}$ to $\bar{\lambda}_{34}$. Likewise, curves 22, 24 and 26 define ISDs from $\bar{\lambda}_{36}$ to $\bar{\lambda}_{38}$, $\lambda_{40}$ to $\lambda_{42}$, and $\lambda_{44}$ to $\bar{\lambda}_{30}$, respectively. Each interval of significant DRP in effect limits the detector response to radiation having wavelengths within the respective interval.

The ISDs are usually defined by the spectral characteristics of the source radiation, by the spectral sensitivity characteristics of the detector, by blocking filters, or combinations thereof. For example, the ISDs for curves 22 and 24 can each be defined by bandpass blocking filters, that is, ones which pass radition within a predetermined wavelength band but which are essentially opaque outside the predetermined wavelength band. Also, an ISD can be established in part by a high pass blocking filter which passes radiation above a predetermined wavelength but blocks radiation (i.e., is essentially opaque) at wavelengths below the predetermined wavelength. For example in FIG. 7, a high pass blocking filter defines the lower portion of the curve 26 and the lower limit $\bar{\lambda}_{44}$. The spectral sensitivity characteristics of the detector defines the upper wavelength portion of the curve 26 and the upper limit $\bar{\lambda}_{30}$. Lastly, no blocking filter may be necessary to define an ISD. For example, the lower portion of the curve 20 and the limit $\bar{\lambda}_{28}$ are defined by the absorbance of oxygen in the optical path while the upper portion of the curve 20 and wavelength $\bar{\lambda}_{34}$ results from the radiation spectral characteristics of the source used for the ISD of curve 20. It is to be noted that an ultraviolet continuum source may be used for the ISD of curve 20 while a tungsten-halogen source may be used for the ISDs of curves 22, 24 and 26.

It is seen that the ISDs overlap to form the instrument wavelength operating range. The portions of the ISDs that actually form the instrument wavelength operating range can be termed a normal wavelength interval (NWI). As the monochromator dial setting is adjusted to wavelengths between $\bar{\lambda}_{28}$ and $\bar{\lambda}_{30}$, the spectrophotometer automatically selects the correct continuum source and blocking filter, if any, for the corresponding NWI. For example, the ultraviolet source with no filter is selected for the curve 20 when the dial setting is between $\bar{\lambda}_{28}$ and a wavelength $\bar{\lambda}_{46}$ at which curves 20 and 22 overlap. The tungsten continuum source with a bandpass blocking filter is selected for the ISD of curve 22 for a NWI between $\bar{\lambda}_{46}$ and $\bar{\lambda}_{47}$. Similarly, NWIs are defined between wavelengths $\bar{\lambda}_{47}$ and $\bar{\lambda}_{48}$, and $\lambda_{48}$ and $\bar{\lambda}_{30}$ for curves 24 and 26 respectively.

In the exemplary embodiment of FIG. 6, the spectrophotometer can include six blocking filters used over a total range of approximately 315 nm to 900 nm. Between 190 and 315 nm, no blocking filter is used. Thus, there are a total of seven ISDs. Such an embodiment is used, for example, in the DU-8 spectrophotometer.

Figure 8:
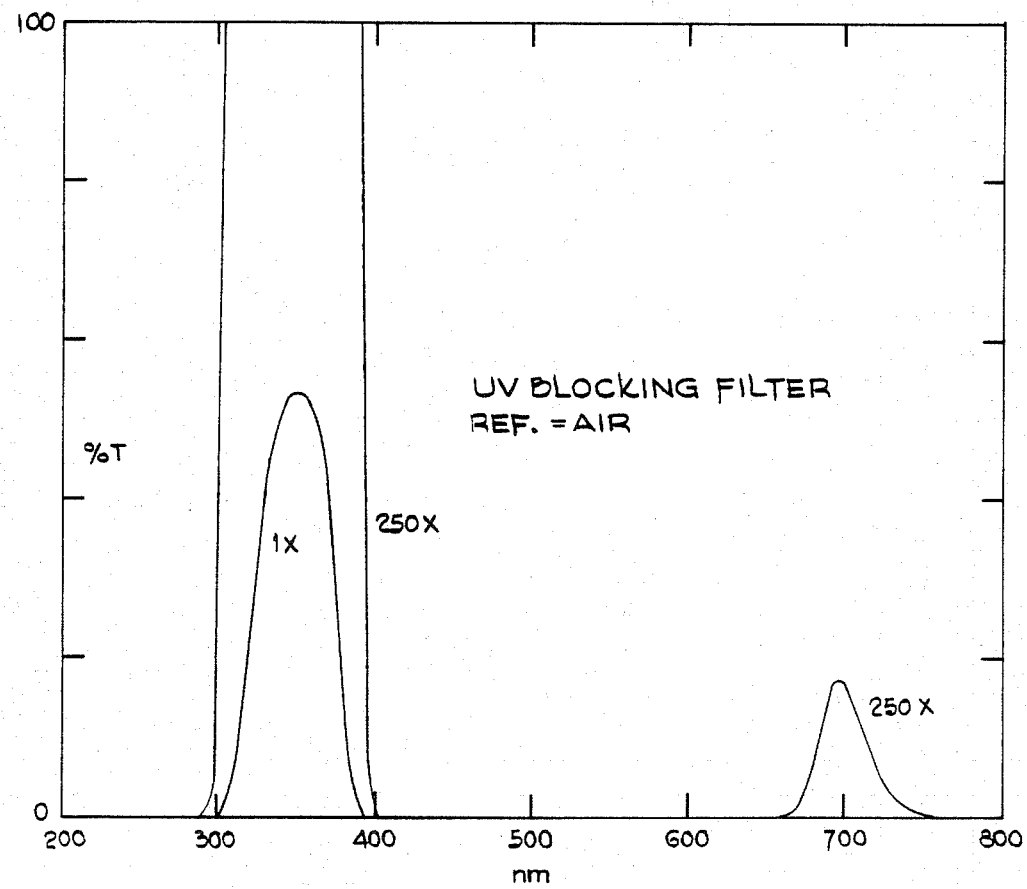
FIG. 8 depicts a transmittance spectrum of a blocking filter employed in the spectrophotometer of FIG. 6.

The blocking filter 92 is an ultraviolet (UV) blocking filter with a transmittance spectrum as shown in FIG. 8. The wavelength range in FIG. 8 between about 325 nm to 385 nm defines the NWI within which the stray light determination is to be made. Of importance, the blocking filter used here is essentially opaque (T less than about $10^{-9}$) at wavelengths shorter than about 290 nm and between about 405 nm and 650 nm. A blocking filter of this nature can comprise a glass filter such as a type U-340 manufactured by Hoya Corp.

In order to obtain the selected DRP spectrum, the monochromator dial setting is varied from, for example, 260 nm to 440 nm and the output from the detector 80 and the preamplifier 84 is recorded by the analog recorder 86. The measured DRP values are then normalized and a curve of the normalized values is plotted. Such a plot is shown as a solid curve 93 in FIG. 9. As is well known to those skilled in the art, the term "normalized" means that the recorded values DRP for curve 93) are adjusted such that the maximum value is equal to unity to thereby provide a more convenient representation of the recorded data.

With respect to the convolution method, "significant DRP" may be considered to be those DRPs which are equal to or greater than about 0.1% of the maximum DRP within the ISD. As seen with reference to curve 93 of FIG. 9, the ISD thereof extends from about 300 nm to about 400 nm. It will be noted that such an interval is somewhat narrower than the interval between the wavelengths at which the blocking filter 92 is essentially opaque (T less than about $10^{-9}$ outside of the interval from about 290 nm to about 405 nm). The ISD need not necessarily extend to such wavelengths because only DRP values which are of significance in evaluating the convolution of Equation (1) need be used.

Figure 9:
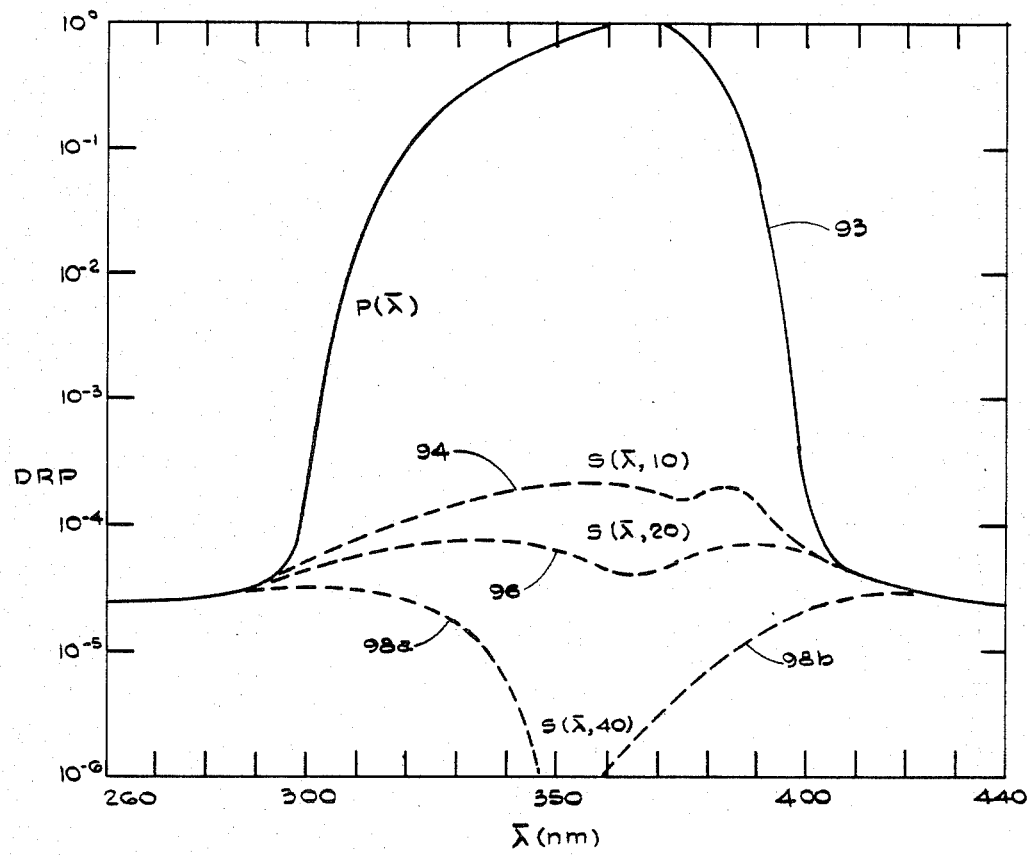
FIG. 9 is a detected radiant power spectrum and stray light spectra for the spectrophotometer of FIG. 6.

The effects of stray light may be seen with reference to FIG. 9. As previously noted, the transmittance of the UV blocking filter 92 is known to be less than about $10^{-9}$ below 290 nm and above 405 nm. Consequently, the observed DRP in these regions in FIG. 9 arises from stray light. That is, even with the monochromator control 73 set to, for example, 270 nm where the primary radiation in the monochromator output beam is completely blocked from the detector 80, stray light generated by the monochromator 72 passes through the blocking filter 92 and results in the DRP shown in FIG. 9 at 270 nm.

Thus, to this point, having determined the slit function of the monochromator 72 and the selected DRP spectrum with the blocking filter 92, the convolution of Equation (1) set forth hereinbefore can be performed to yield stray light measurement.

Two examples of the convolution will now be presented. Such examples assume that a holographic grating is used in the disperser of the monochromator 72.

The first convolution is performed for the purpose of evaluating K as shown in Equation (1).

To determine the constant K, a convolution is performed at a wavelength at least about 30 nm away from the interval of significant DRP within which the stray light measurement is to be made.

With the wavelength selected to be 30 nm outside of the ISD, no primary radiation is detected by the detector and thus the resulting DRP must arise from stray light of wavelengths within the ISD.

To perform the convolution, it is first necessary to calculate values for n for the summation of Equation (1). The selected DRP spectrum $P(\bar{\lambda}-n\Delta)$ will have a significant magnitude only for $\lambda$ values between 300 and 400 nm. Using Equation (2) and solving for n, it is found that n ranges from $-6$ to $-26$ ($\lambda=300$ nm to $\lambda=400$ nm, respectively) where $\Delta$ equals 5 and $\bar{\lambda}$ equals 270 nm. The slit functions will then range over values of $\lambda-\bar{\lambda}=-30$ to $\bar{\lambda}-\lambda=-130$ nm. From FIG. 3, it is seen that significant slit function data exists over such an interval.

The increment $\Delta$ is selected as a compromise between accuracy of the resulting summation and the time required to calculate the products comprising the summation. It is apparent that as $\Delta$ becomes smaller, the accuracy of the summation increases. However, the amount of increase in accuracy becomes less as $\Delta$ approaches relatively small numbers. Here, $\Delta=5$ provides a reasonable summation accuracy yet requires a manageable number of products (21) to be calculated. Variations in $\Delta$ will be further apparent to those skilled in the art.

The summation is shown in Table 1 which shows the corresponding P and F functions.

TABLE 1

$\bar{\lambda}=270$ nm
$\Delta=5$ nm
n range: $-26$ to $-6$

| n | $n\Delta$ | $\bar{\lambda}-n\Delta$ | $P(\bar{\lambda}-n\Delta)$ | $F(n\Delta)$ | $P(\bar{\lambda}-n\Delta)F(n\Delta)$ |
|---|---|---|---|---|---|
| $-26$ | $-130$ | 400 | $1.7\times10^{-4}$ | $1.60\times10^{-6}$ | $2.72\times10^{-10}$ |
| $-25$ | $-125$ | 395 | $4.0\times10^{-3}$ | $1.61\times10^{-6}$ | $6.44\times10^{-9}$ |
| $-24$ | $-120$ | 390 | $5.0\times10^{-2}$ | $1.62\times10^{-6}$ | $8.10\times10^{-8}$ |
| $-23$ | $-115$ | 385 | $2.2\times10^{-1}$ | $1.64\times10^{-6}$ | $3.61\times10^{-7}$ |
| $-22$ | $-110$ | 380 | $4.8\times10^{-1}$ | $1.66\times10^{-6}$ | $7.97\times10^{-7}$ |

TABLE 1-continued $\bar{\lambda}=270$ nm
$\Delta=5$ nm
n range: $-26$ to $-6$

| n | $n\Delta$ | $\bar{\lambda}-n\Delta$ | $P(\bar{\lambda}-n\Delta)$ | $F(n\Delta)$ | $P(\bar{\lambda}-n\Delta)F(n\Delta)$ |
|---|---|---|---|---|---|
| $-21$ | $-105$ | 375 | $7.7\times10^{-1}$ | $1.68\times10^{-6}$ | $1.29\times10^{-6}$ |
| $-20$ | $-100$ | 370 | $9.6\times10^{-1}$ | $1.70\times10^{-6}$ | $1.63\times10^{-6}$ |
| $-19$ | $-95$ | 365 | $1.0$ | $1.73\times10^{-6}$ | $1.73\times10^{-6}$ |
| $-18$ | $-90$ | 360 | $9.5\times10^{-1}$ | $1.75\times10^{-6}$ | $1.66\times10^{-6}$ |
| $-17$ | $-85$ | 355 | $8.6\times10^{-1}$ | $1.77\times10^{-6}$ | $1.52\times10^{-6}$ |
| $-16$ | $-80$ | 350 | $7.2\times10^{-1}$ | $1.81\times10^{-6}$ | $1.30\times10^{-6}$ |
| $-15$ | $-75$ | 345 | $6.0\times10^{-1}$ | $1.85\times10^{-6}$ | $1.11\times10^{-6}$ |
| $-14$ | $-70$ | 340 | $4.7\times10^{-1}$ | $1.92\times10^{-6}$ | $9.0\times10^{-7}$ |
| $-13$ | $-65$ | 335 | $3.7\times10^{-1}$ | $1.99\times10^{-6}$ | $7.36\times10^{-7}$ |
| $-12$ | $-60$ | 330 | $2.6\times10^{-1}$ | $2.15\times10^{-6}$ | $5.59\times10^{-7}$ |
| $-11$ | $-55$ | 325 | $1.8\times10^{-1}$ | $2.3\times10^{-6}$ | $4.14\times10^{-7}$ |
| $-10$ | $-50$ | 320 | $1.08\times10^{-1}$ | $2.6\times10^{-6}$ | $2.81\times10^{-7}$ |
| $-9$ | $-45$ | 315 | $5.0\times10^{-2}$ | $2.9\times10^{-6}$ | $1.45\times10^{-7}$ |
| $-8$ | $-40$ | 310 | $1.8\times10^{-2}$ | $3.4\times10^{-6}$ | $6.12\times10^{-8}$ |
| $-7$ | $-35$ | 305 | $3.0\times10^{-3}$ | $4.5\times10^{-6}$ | $1.35\times10^{-8}$ |
| $-6$ | $-30$ | 300 | $3.0\times10^{-4}$ | $5.7\times10^{-6}$ | $1.71\times10^{-9}$ |
| | | | | Sum: | $1.46\times10^{-5}$ |

$$K = \frac{2.6\times10^{-5}}{1.46\times10^{-5}} = 1.78$$

The summation shown in Table 1 corresponds to $K\times S(270, L>30)$. Because the DRP at 270 nm is directly equal to $S(270, L>30)$, K must be equal to the DRP at 270 divided by the summation result shown in Table 1. The K value thus determined is independent of $\bar{\lambda}$. With K now known, the convolution summation can be determined for any value of $\bar{\lambda}$.

As a second example of the convolution of Equation (1), the convolution can be performed to determine stray light ratio (SLR) at 350 nm.

In order to determine the stray light ratio at 350 nm, the stray light $S(350, L)$ must first be determined. Consequently, a value for L must be specified.

There are essentially two restriction on the values of L. The first restriction relates to the minimum value thereof and the second restriction relates to the maximum value.

With respect first to the minimum value for the limit L, such minimum value is imposed by the monochromaticity of the radiation used in determining the slit function. In the embodiment disclosed herein, transmission characteristics of the isolation filter or fiters is the most important factor influencing the monochromaticity of the radiation. Theoretically, the slit function is presumed to be proportional to the transmittance of the monochromator for radiation of a single wavelength, that is, monochromatic. In practice, however, the monochromatic radiation has a finite width and stray light measurements in accordance with the convolution method disclosed herein cannot be determined for L values smaller than the half bandwidth of such radiation. For example, isolation filters having half bandwidths of approximately 3 nm for visible radiation and 10 nm for ultraviolet radiation are readily available. Thus, such numbers substantially represent the minimum L values usable with such filters. Where smaller L values are desired, it is necessary to correct for continuum radiation near the monochromatic radiation wavelength. For the embodiment disclosed herein, such a correction may be made using the source spectrum of FIG. 3 and the transmittance spectra for the isolation filters 74 and 76 of FIG. 4. A correction of this nature will be readily apparent to those skilled in the art.

The second restriction relating to the value of L concerns the maximum value thereof. For a measure of stray light for use in an instrument specification, the value of L may be somewhat arbitrary and should be indicated as a part of the instrument specification. Here, a value of L equal to 15 is grater than the half bandwidth of the monochromatic radiation used to determine the slit function and is less than 30 nm, the minimum number of nanometers away from the ISD at which K is determined as described above.

With a sample in the beam, the maximum value of L is related to the absorptive characteristics of the sample. The selection of L with a sample in the beam is discussed more fully hereinbelow.

The n values again must be calculated in the same manner as in the first example. With the blocking filter 92 in place, the function $P(\overline{\lambda}-n\Delta)$ has a significant magnitude for wavelengths between 300 and 400 nm. This is to say that the DRP spectrum $P(\overline{\lambda}-n\Delta)$ has a significant interval of DRP between 300 and 400 nm. Consequently, n ranges from $-10$ to $+10$ but excludes values corresponding to the interval of primary radiation, that is, the interval defined by L. Thus, values of n between $-L/\Delta=-3$ and $+L/\Delta=+3$ must be omitted.

The following Table 2 lists the P and F values for n of $-10$ to $-3$ and from $+3$ to $+10$ along with the products thereof and the resulting summation.

TABLE 2

$\overline{\lambda} = 350$ nm
$\Delta = 5$ nm
n range: $-10$ to $-3$ and 3 to 10

| n | n$\Delta$ | $\overline{\lambda}-n\Delta$ | $P(\overline{\lambda}-n\Delta)$ | $F(n\Delta)$ | $P(\overline{\lambda}-n\Delta)F(n\Delta)$ |
|---|---|---|---|---|---|
| −10 | −50 | 400 | $1.7 \times 10^{-4}$ | $2.6 \times 10^{-6}$ | $4.42 \times 10^{-10}$ |
| −9 | −45 | 395 | $4.0 \times 10^{-3}$ | $2.9 \times 10^{-6}$ | $1.16 \times 10^{-8}$ |
| −8 | −40 | 390 | $5.0 \times 10^{-2}$ | $3.4 \times 10^{-6}$ | $1.70 \times 10^{-7}$ |
| −7 | −35 | 385 | $2.2 \times 10^{-1}$ | $4.5 \times 10^{-6}$ | $9.9 \times 10^{-7}$ |
| −6 | −30 | 380 | $4.8 \times 10^{-1}$ | $5.7 \times 10^{-6}$ | $2.74 \times 10^{-6}$ |
| −5 | −25 | 375 | $7.7 \times 10^{-1}$ | $7.8 \times 10^{-6}$ | $6.01 \times 10^{-6}$ |
| −4 | −20 | 370 | $9.6 \times 10^{-1}$ | $12.0 \times 10^{-6}$ | $1.15 \times 10^{-5}$ |
| −3 | −15 | 365 | 1.0 | $18.5 \times 10^{-6}$ | $1.85 \times 10^{-5}$ |
| 3 | 15 | 335 | $3.7 \times 10^{-1}$ | $17.0 \times 10^{-6}$ | $6.29 \times 10^{-6}$ |
| 4 | 20 | 330 | $2.6 \times 10^{-1}$ | $11.2 \times 10^{-6}$ | $2.91 \times 10^{-6}$ |
| 5 | 25 | 325 | $1.8 \times 10^{-1}$ | $7.4 \times 10^{-6}$ | $1.33 \times 10^{-6}$ |
| 6 | 30 | 320 | $1.08 \times 10^{-1}$ | $5.5 \times 10^{-6}$ | $5.94 \times 10^{-7}$ |
| 7 | 35 | 315 | $5.0 \times 10^{-2}$ | $4.4 \times 10^{-6}$ | $2.20 \times 10^{-7}$ |
| 8 | 40 | 310 | $1.8 \times 10^{-2}$ | $3.2 \times 10^{-6}$ | $5.76 \times 10^{-8}$ |
| 9 | 45 | 305 | $3.0 \times 10^{-3}$ | $2.8 \times 10^{-6}$ | $8.4 \times 10^{-9}$ |
| 10 | 50 | 300 | $3.0 \times 10^{-4}$ | $2.5 \times 10^{-6}$ | $7.5 \times 10^{-10}$ |
| | | | | Sum: | $5.13 \times 10^{-5}$ |

$S(350,15) = (5.13 \times 10^{-5}) \times (1.78) = 9.14 \times 10^{-5}$

The summation multiplied by the above determined K value is equal to S(350, 15), or $9.14 \times 10^{-5}$.

To determine the stray light ratio at 350 nm, the stray light as just determined is divided by the DRP at 350 nm. The DRP at 350 nm is determined from FIG. 9 and is 0.72. The resulting calculation yields a SLR equal to about $1.27 \times 10^{-4}$.

Although "significant DRP" has been termed herein to be those DRPs which are equal to or greater than about 0.1% of the maximum DRP within the ISD, such a definition must be tempered by the contribution a DRP value makes to a stray light measurement. For example, as seen in Table 2, the products of the slit function and the selected DRP spectrum for $n=-10$, $n=9$, and $n=10$ do not contribute to the value of the stray light S(350,15) when expressed in three significant figures. Thus, the ISD may be considered to be somewhat narrower for such a calculation (310 nm to 395 nm).

The convolution can be performed at a plurality of wavelengths $\overline{\lambda}$ and for various values of L. The results of three such determinations are illustrated in FIG. 9 as shown by stray light spectra dashed lines 94, 96 and 98a, 98b. Stray light spectra can be determined as the ratios between the dashed line stray light spectra 94, 96 and 98a, 98b of FIG. 9 and the selected DRP spectrum shown in the solid curve 93 of FIG. 9.

As seen with reference to FIG. 5, several additional slit functions are illustrated therein for different wavelengths of monochromatic radiation. Curves 88b illustrate a slit function for 254 nm, curves 88c illustrate a slit function for 436 nm, and curve 88d is a slit function for 546 nm. It is thus seen that such slit functions vary slightly with the wavelength of the monochromatic radiation. Within an ISD, such a variation is relatively insignificant. For high accuracy, it is desirable to determine a slit function for each ISD with each slit function determined using monochromatic radiation with a wavelength somewhere within the respective ISD. The convolution described herein is then performed for the selected DRP spectrum and the slit function determined using monochromatic light having a wavelength within the ISD of the selected DRP spectrum.

It is to be understood that the convolution of Equation (1) may be performed by any conventional means. For example, in the embodiment disclosed herein, the calculations of Tables 1 and 2 were conveniently performed by a programmable calculator. However, the determination of stray light and SLRs may also be performed using a computer. In an automated, microprocessor-based spectrophotometer, such determinations can be performed by the microprocessor therein using programming techniques that are well known in the art. With such an instrument, the slit function and the selected DRP spectrum may be digitized and stored as a plurality of values.

Although the above examples have been directed to stray light determinations as an indication of instrument performance, the present method is also capable of stray light measurement with the sample in the beam. Because of this, such a method is uniquely and advantageously adaptable to correcting a sample transmittance or absorbance measurement for the influence of stray light. Such compensation with reasonable accuracy has been heretofore impossible and thus the present method provides a greatly improved measurement accuracy, particularly where sample transmittance is relatively low, for example, less than about $10^{-2}$.

Generally, such a stray light measurement method uses a slit function as described hereinbefore. However, the selected DRP spectrum $P(\overline{\lambda}-n\Delta)$ is determined at least through the ISD with a sample in the beam. Convolutions of the selected DRP spectrum with the slit function are then formed to provide a stray light measurement.

Figure 10A:
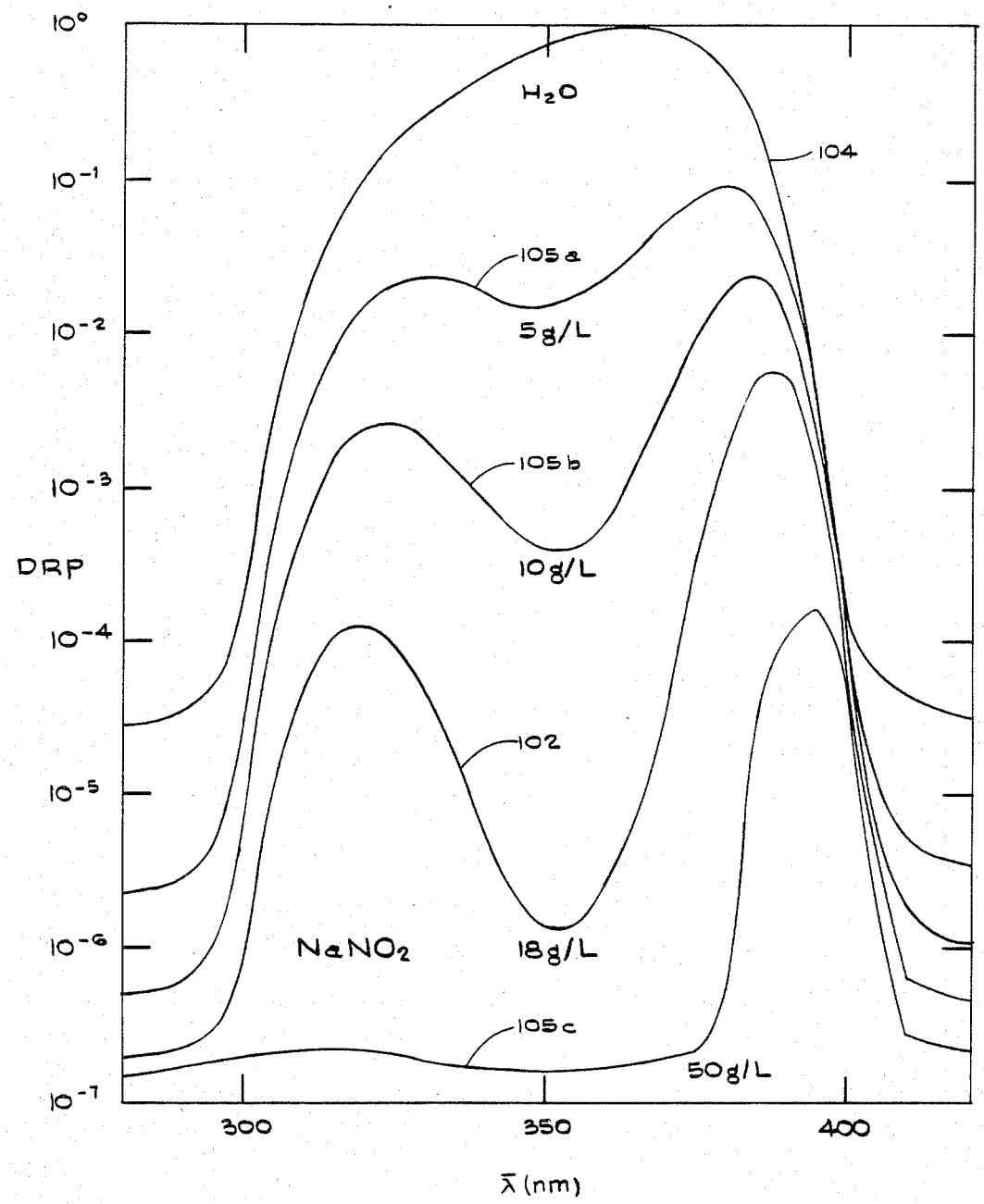
FIG. 10A depicts detected radiant power spectra and stray light spectra with several samples in the beam of the spectrophotometer of FIG. 6.

As an example of the present convolution method with a sample in the beam, a sample 100 (FIG. 6) is placed within the sample compartment 78 and in the path of the beam from the monochromator 72 to the detector 80. The sample 100 may be a sample of a one centimeter path length 18 g/L solution of $NaNO_2$. With the sample 100 in the beam, a selected DRP spectrum as seen by curve 102 of FIG. 10A is measured at least over the interval of significant DRP (ISD), it is to be noted that the ISD is determined by the blocking filter 92. However, it is seen that the sample 100 substantially influences the resulting selected DRP spectrum 102 as compared to the instrument DRP spectrum shown by the curve 93 in FIG. 9. The curve 102 in FIG. 10A is normalized as is well known in the art with respect to a reference DRP spectrum also measured over the ISD. The reference DRP spectrum is measured with only the solvent in the beam. Such a reference DRP spectrum is seen in FIG. 10 as curve 104. By normalized as used here, it is meant that the reference spectrum 104 and the selected DRP spectrum 102 are multiplied by a factor that sets the maximum value of the reference DRP spectrum 104 equal to unity. Other examples of selected DRP spectra are shown by curves 105a, 105b and 105c of FIG. 10A for 1 cm path length solutions of $NaNO_2$ having concentrations of 5 g/L, 10 g/L, and 50 g/L, respectively.

With the monochromator slit function as shown by curves 88a (measured for 334 nm monochromatic light) and the selected DRP spectrum 102 of FIG. 10A, the proportionality constant K of Equation (1) may be determined. Such a determination is similar to that illustrated in detail above with reference to Table 1. However, the selected DRP spectrum is now the curve 102 of FIG. 10A. To determine the constant K, a summation in accordance with Equation (1) is performed for a wavelength outside the range of significant DRP. As in the previous example of Table 1, such a wavelength can be $\bar{\lambda}=270$ nm. The summation range for n is again calculated to be $-26$ to $-6$ as before.

The summation is then performed and, as previously described, the proportionality constant K is found such that the product of the proportionality constant K and the summation for $\bar{\lambda}=270$ nm is equal to the measured DRP of curve 102 at 270 nm. From FIG. 10A, it is seen that the DRP at 270 nm is approximately $1.7 \times 10^{-7}$. K is then accordingly determined.

With K found for the DRP spectrum 102, the stray light for various wavelengths within the ISD can be determined. For example, for a wavelength $\bar{\lambda}=350$ nm, the summation values for n are determined as above to be $-10$ to 10, subject to value of the limit L desired.

The minimum value of L is determined as described above with respect to the isolation filter or filters transmission characteristics. The maximum value of L should be less than the half bandwidth of the sample absorption band within which the stray light corrected sample measurement is to be made. Such a limitation for L is based on a presumption that most of the stray light of wavelengths within such half bandwidth will be absorbed. Consequently, the stray light determined using the present convolution will be independent of L where L is less than the half bandwidth of the sample absorption band under investigation. Such a presumption of relatively strong sample absorption is, in practice, seldom restricting because the error in measured sample transmittance resulting from stray light is significant only at relatively low values (less than about $10^{-2}$) of transmittance.

For the DRP spectrum 102 of FIG. 10A, an L of 15 meets the requirements just described. Thus, values of n between $-L/\Delta = -3$ and $L/\Delta = 3$ must be omitted.

With $\bar{\lambda}$, K, L, and n known, and again assuming $\Delta$ equals 5 nm, a summation similar to that shown in Table 2 is then performed. The resulting summation is multiplied by K to yield $S(350, 15) = 7 \times 10^{-7}$.

Figure 10B:
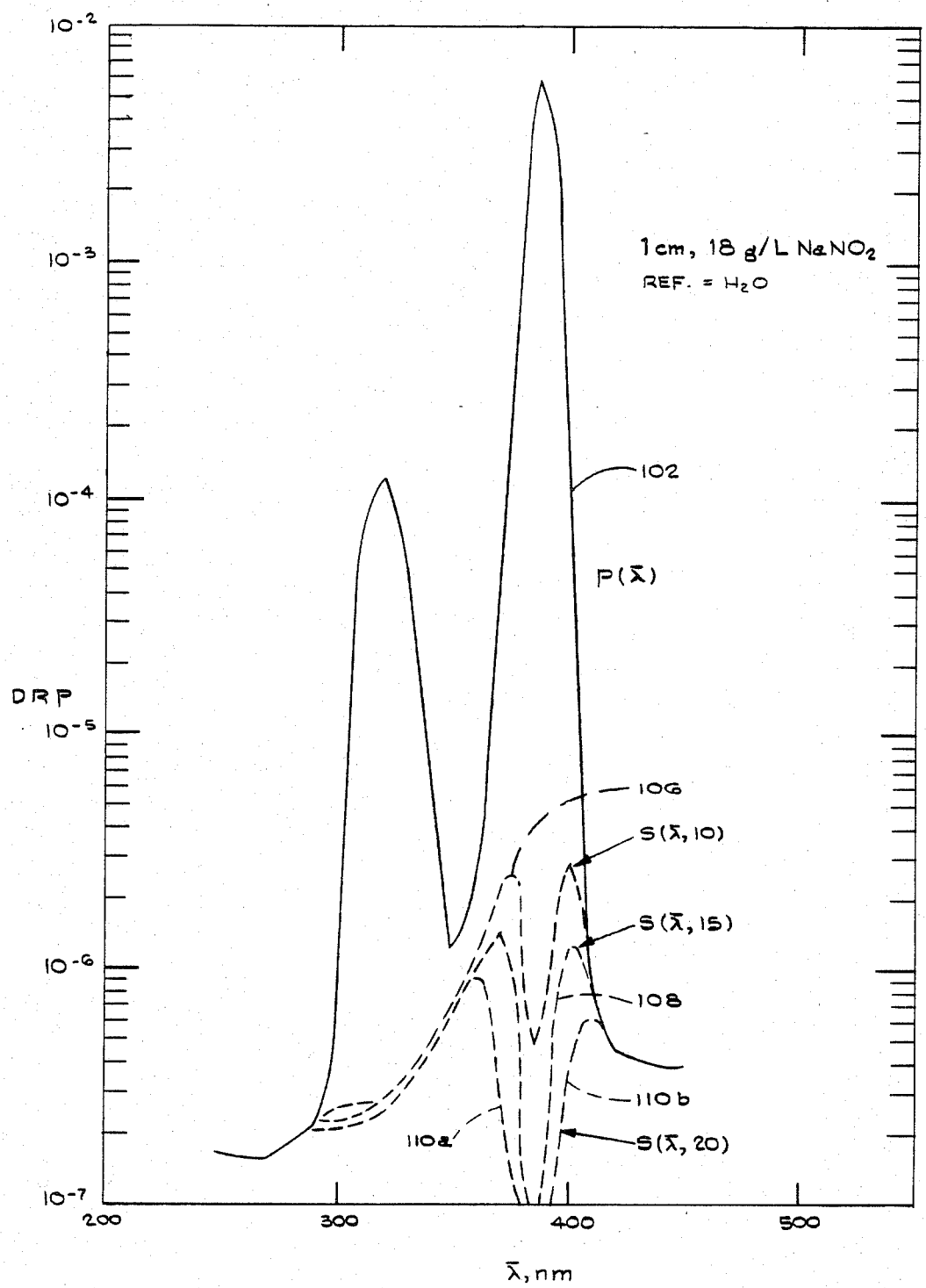
FIG. 10B depicts the selected detected radiant power spectra of FIG. 10A and stray light spectra.

The stray light may be calculated for a plurality of wavelengths λ in accordance with the convolution of the present invention. Curves 106, 108 and 110a, 110b of FIG. 10B depict stray light spectra so calculated. It is to be noted that the stray light is a large fraction of the DRP at approximately 350 nm, that is, where the sample $NaNO_2$ absorbs most of the radiant power. The curves 106–110a, 110b are for varying values of L similar to the curves 94, 96 and 98a, 98b of FIG. 9 where no sample was in the beam.

Moreover, the stray light spectra shown in FIG. 10B can be used as previously described to determine SLR. In such an instance, the SLR for a particular value of L is the ratio of the respective dashed curve 106, 108 or 110a, 110b to the reference DRP spectrum 104.

Advantageously, a sample transmittance measurement corrected for stray light in accordance with the present invention can be found with the following relationship:

$$T_\lambda^{sample\ corrected} = \frac{DRP_\lambda^{sample} - S_{(\bar{\lambda},L)}^{sample}}{DRP_\lambda^{reference}} \quad \text{(Eq. 7)}$$

where
$T_\lambda^{sample\ corrected}$ is sample transmittance corrected for stray light at wavelength λ;
$DRP_{\bar{\lambda}}^{sample}$ is the uncorrected sample DRP at wavelength $\bar{\lambda}$;
$S(\bar{\lambda},L)^{sample}$ is the sample stray light determined in accordance with the method of the present invention; and
$DRP_{\bar{\lambda}}^{reference}$ is the DRP of the reference at wavelength $\bar{\lambda}$. Carrying on the foregoing example, for a 1 cm path length sample of 18 g/L $NaNO_2$ at $\bar{\lambda}=350$ nm, the $DRP_{\bar{\lambda}}^{sample}$ is found from the curve 102 of FIG. 10. The sample stray light is found as just described. The $DRP_{\bar{\lambda}}^{reference}$ is obtained from the curve 104 at $\bar{\lambda}=350$ nm.

Substituting the values into equation (7), the corrected transmittance is:

$$\frac{1.5 \times 10^{-6} - 7 \times 10^{-7}}{0.9} = 8.9 \times 10^{-7}$$

Thus the convolution method in accordance with the present invention provides relatively accurately compensated transmittance and absorbance measurements for samples.

The stray light measurement and compensation methods disclosed herein are influenced by the type of disperser used in the monochromator. For example, gratings prepared by a holographic process generally exhibit slit functions of the type seen in FIG. 3 and all methods disclosed herein including the simplified method disclosed hereinbelow are directly usable.

However, gratings prepared by mechanical ruling techniques exhibit slit functions characterized by "ghost" spectral lines with DRPs rising abruptly by factors of 1 to 100. The convolution method disclosed herein tends to broaden such ghosts until they are as wide as the ISD. However, ruled gratings may be used with the present convolution method where $|\bar{\lambda} - \lambda|$ for the first prominent ghost in the ruled grating slit function is greater than the width of the ISD used for the convolution. Where $|\bar{\lambda} - \lambda|$ for the first prominent ghost is less than the interval of the ISD used for the convolution, the covolution may still be used but the accuracy of the resulting stray light or SLR measurement may be reduced. However, a modified method as is described hereinbelow which does not require a convolution may be substantially affected by such a ghost.

Thus, the following modified method is preferably performed with monochromators using holographic gratings.

Although the convolution method just described provides an accurate measurement of stray light and, in particular, stray light with a sample in the beam, a modified method of compensation in accordance with the present invention can also be performed while still providing good results. Such a modified test requires no convolution or slit function measurement and therefore considerably simplifies the task of determining corrected sample transmittance.

Generally, in such a method which is sometimes referred to hereinafter as the "blocking filter method", DRP measurements are made with the reference and the sample in the beam at the wavelength of interest, here denoted $\bar{\lambda}_1$. Each such DRP measurement is performed within the ISD normally used at $\bar{\lambda}_1$. As used with respect to the blocking filter method, the ISD is generally as previously described with respect to FIG. 7. For the purpose of the present description of the blocking filter method, the ISD may be considered to limit detector response to radiation having wavelengths within the respective interval. Stated somewhat differently, radiation having wavelengths outside the ISD produces essentially no DRP.

With the sample still in the beam, the monochromator dial setting is adjusted to a value $\bar{\lambda}_2$ outside the ISD originally selected. The dial setting $\bar{\lambda}_2$ is selected such that the DRP is produced essentially only in response to stray light. For example, where a blocking filter defines the ISD within which $\bar{\lambda}_1$ lies, $\bar{\lambda}_2$ is selected to be outside the ISD at a wavelength where the blocking filter is essentially opaque. Consequently, radiation in the monochromator output beam which may be considered to be other than stray light is blocked from the detector.

At $\bar{\lambda}_2$, another DRP measurement is made. Transmittance for the sample corrected for the influence of stray light is then calculated in accordance with the following Equation (3):

$$T_{\bar{\lambda}_1}^{sample\ corrected} = \frac{DRP_{\bar{\lambda}_1}^{sample} - DRP_{\bar{\lambda}_2}^{sample}}{DRP_{\bar{\lambda}_1}^{reference}} \quad (Eq.\ 3)$$

where
$T_{\bar{\lambda}_1}^{sample\ corrected}$ is sample transmittance corrected for stray light at wavelength $\bar{\lambda}hd\ 1$;
$DRP_{\bar{\lambda}_1}^{sample}$ is the uncorrected sample DRP at wavelength $\bar{\lambda}_1$;
$DRP_{\bar{\lambda}_2}^{sample}$ is the sample DRP at wavelength $\bar{\lambda}_2$; where $\bar{\lambda}_2$ is a wavelength outside the ISD used for $\bar{\lambda}_1$ and at which radiation with a wavelength equal to $\bar{\lambda}_2$ produces essentially no DRP; and
$DRP_{\bar{\lambda}_1}^{reference}$ is the DRP of the reference at wavelength $\lambda_1$.

Using the blocking filter method, the corrected sample transmittance at 350 nm can be determined with reference to FIG. 10. The quantity $$DRP_{\bar{\lambda}_1}^{sample}$$

is found from curve 102 at 350 nm and equals $1.5 \times 10^{-6}$. Similarly, the $$DRP_{\bar{\lambda}_2}^{sample}$$

is found with reference to curve 104 at 290 nm and equals $4 \times 10^{-7}$. Lastly, the value of $$DRP_{\bar{\lambda}_1}^{reference}$$

is found from curve 104 from FIG. 10 at 350 nm to be 0.9 Substituting the values into Equation (3), the sample transmittance corrected for stray light is:

$$\frac{1.5 \times 10^{-6} - 4 \times 10^{-7}}{0.9} = 1.2 \times 10^{-6}$$

It is to be noted that the wavelength of $\bar{\lambda}_2$ is chosen to be 290 nm because, at that wavelength, the blocking filter 92 (FIG. 7) is essentially opaque as seen with reference to FIG. 8. Thus, the DRP at the monochromator dial setting wavelength $\bar{\lambda}_2$ can be assumed to arise from stray light having wavelengths within the ISD in the presence of the sample.

It is to be noted that the transmittance corrected using the convolution method as described hereinbefore is smaller than that obtained using the simpler method including Equation (3). This is partly because the simpler method does not specify a limit L as found in the convolution Equation (1).

Also, the present novel blocking filter correction method assumes that the stray light throughout the interval of significant DRP (300 nm to 400 nm as seen in FIG. 10A) is substantially constant. Although such an assumption is not as accurate as the convolution method described above, the ISD transmittance correction method is still more accurate than uncorrected transmittance. For example, here such uncorrected transmittance is $1.5 \times 10^{-6}/0.9 = 1.7 \times 10^{-6}$.

It should also be noted that the example described hereinabove for the 18 g/L solution of $NaNO_2$ attempts to measure an extremely small transmittance (about $1 \times 10^{-6}$), a rather extreme illustration. In spite of this, however, sample transmittance may be measured and corrected for stray light using either the convolution method or the blocking filter method as disclosed herein to thereby provide a more accurate indication of transmittance.

Although the present simpler method is referred to herein as the blocking filter method, the ISD within which $\bar{\lambda}_1$ lies may not be defined by a blocking filter but instead by other suitable means. For example, an ISD over an interval of ultraviolet wavelengths may be defined by the absorbance properties of oxygen in the optical path and the spectral radiation characteristics of the source. Such an example is described hereinbefore with reference to curve 20 of FIG. 7. For the present method, $\bar{\lambda}_1$ would be selected between $\bar{\lambda}_{28}$ and $\bar{\lambda}_{46}$ of FIG. 7 and $\bar{\lambda}_2$ would be selected at a wavelength shorter than $\bar{\lambda}_{28}$. Those skilled in the art will recognize other suitable means equivalent to those described herein.

The relationship set forth herein as Equation (3) may be implemented in a number of equivalent methods and such implementations are not to detract from the scope of the appended claims. Moreover, such a transmittance correction method may be implemented by modifying an automated spectrophotometer such as the Model DU-8 spectrophotometer. The instrument is controlled by means of a microprocessor and sample measurements corrected for stray light may be obtained using the following method. It is to be noted that the following method calculates absorbance corrected for stray light.

However, those skilled in the art will recognize that absorbance is simply related to transmittance as set forth hereinbefore. Thus, the present example merely is one illustration of methods equivalent to the present invention.

In an exemplary modified DU-8 instrument, sample measurements corrected for stray light are only made when the instrument is operated in an absorbance mode. Such an implementation is necessary because of the resolution of a digitization process within the instrument which converts an analog DRP signal into a resulting digital representation. Of course, transmittance values corrected for stray light may always be calculated from the corrected absorbance measurements.

To perform the correction method, a reference is first placed into the instrument sample compartment in the monochromator output beam. The instrument then measures and records the logarithm of the reference DRP at the wavelength of interest. For example, assuming again that the wavelength selected is 350, the spectrophotometer automatically selects the appropriate UV blocking filter 92 as seen in FIG. 7 to define the ISD within which the dial setting 350 nm lies.

With the reference logarithmic DRP stored, the sample is then inserted into the sample compartment in the monochromator output beam. The instrument then measures the log DRP of the sample and the value is stored.

It should be noted that the difference between the two stored logarithmic values corresponds to the uncorrected absorbance of the sample at 350 nm. Furthermore, at this point, it is seen that the spectrophotometer operates in a conventional fashion to provide an absorbance measurement. The uncorrected absorbance measurement is mathematically converted into an uncorrected transmittance by the microprocessor within the instrument. The uncorrected sample transmittance is stored.

To complete the blocking filter method, the monochromator dial setting is next changed to 290 nm. As previously described, such a dial setting is outside the ISD defined by the blocking filter 92. Importantly, the blocking filter 92 is essentially opaque at 290 nm. However, the spectrophotometer does not select another blocking filter or source which would otherwise be used to define the ISD normally used at 290 nm. Instead, the blocking filter 92 remains in the monochromator output beam.

With the monochromator dial setting at 290 nm, the logarithmic DRP of the sample is again measured. It will be understood that it may be necessary to increase the sensitivity of the detector as, for example, by varying the dynode voltage thereof where the detector is a photomultiplier tube.

It will also be recognized that the log DRP at 290 nm may be considered to be equal to the log DRP at 350 nm which arises solely from stray light in the presence of the sample. Moreover, the difference between the log DRP at 290 nm and the log DRP at 350 nm for the reference can be considered as an absorbance equivalent of the sample arising solely from stray light at a dial setting of 350 nm.

To perform the compensation, the absorbance equivalent just described is converted by the spectrophotometer microprocessor mathematically into a stray light transmittance equivalent. The difference between the uncorrected sample transmittance at 350 nm and the stray light transmittance equivalent (in the presence of the sample) is equal to the corrected transmittance of the sample. The spectrophotometer then converts the resulting corrected transmittance into absorbance and prints the value.

Although a particular embodiment of the blocking filter method has just been described, it is to be noted that various spectrophotometer instruments may perform such a method as disclosed herein in a number of equivalent ways.

Thus, the stray light mesurement and compensation techniques set forth herein provide relatively accurate measurements of stray light and furthermore advantageously and uniquely allow sample measurements to be corrected for stray light. Such a correction is extremely desirable in the field of spectroscopy and provides results more accurate than heretofore uncorrected measurements, particularly with single monochromator instruments. By measuring and correcting for stray light with the sample in the beam, the effective accuracy and range of a spectrophotometer is expanded.

Although an exemplary method in accordance with the present invention has been set forth herein, those skilled in the art will recognize numerous equivalents thereto. Such equivalents and other modifications may be made without departing from the scope and spirit of the appended claims.

What is claimed is:

1. A method for determining stray light in a spectrophotometer at a first wavelength where the spectrophotometer has an optical path including a monochromator generating an output beam having a central wavelength and a predetermined slit function, a detector positioned to receive radiation from the monochromator, and means for substantially limiting detector response to radiation within an interval of significant detected radiant power, the interval of significant detected radiant power including the first wavelength, the method comprising the steps of:
    (a) measuring a detected radiant power spectrum for a range of central wavelengths including at least the interval of significant detected radiant power,
    (b) summing the product of the slit function and the detected radiant power spectrum over a first range of summation wavelengths including at least the interval of significant detected radiant power, but not including wavelengths within a predetermined interval around the first wavelength, and
    (c) scaling the result of step (b) by a constant to determine stray light, the constant having a value such that a summation of the products of the slit function and the detected radiant power spectrum over a second range of summation wavelengths including at least the interval of significant detected radiant power, when scaled by the constant, is equal to a detected radiant power at a second wavelength outside the interval of significant detected radiant power.

2. The method of claim 1 wherein the spectrophotometer includes sample receiving means adapted to receive a sample such that the sample is in the optical path, and wherein step (a) comprises measuring the detected radiant power spectrum with a sample in the optical path such that the detected radiant power spectrum includes a detected radiant power at the first wavelength.

3. The method of claim 2 further including
    (d) subtracting the stray light determined by step (c) from the detected radiant power at the first wavelength to determine a detected radiant power at the first wavelength compensated for stray light;

(e) measuring a detected radiant power without a sample in the optical path at the first wavelength; and (f) dividing the result of step (d) by the result of step (e) to determine sample transmittance at the first wavelength corrected for stray light.

4. The method of claim 1 further including (d) determining a detected radiant power at the first wavelength, and (e) forming a ratio of the result of step (c) to the detected radiant power of step (d) to determine a stray light ratio.

5. The method of claim 2 further including (d) measuring a detected radiant power without the sample in the optical path at the first wavelength, and (e) forming a ratio of the result of step (c) to the detected radiant power of step (d) to determine a stray light ratio.

6. The method of claim 1 wherein step (b) includes selecting the slit function value for each product according to the difference between the first wavelength and the summation wavelength for the respective product.

7. The method of claim 6 wherein the slit function value for each product of step (c) is selected according to the difference between the first wavelength and the summation wavelength for the respective product.

8. A convolution method for determining stray light in a spectrophotometer at a first wavelength where the spectrophotometer has an optical path including a monochromator generating an output beam having a central wavelength and having a predetermined slit function, a detector positioned to receive radiation from the monochromator, and means for substantially limiting detector response to radiation having wavelengths within an interval of significant detected radiant power, the interval of significant detected radiant power including the first wavelength, the method comprising the steps of:

(a) measuring a detected radiant power spectrum for a range of central wavelengths including at least the interval of significant detected radiant power;

(b) measuring a detected radiant power at a second wavelength outside the interval of significant detected radiant power;

(c) selecting a first plurality of summation wavelengths over a range of wavelengths including at least the interval of significant detected radiant power;

(d) summing the products of the slit function and the detected radiant power spectrum for the first plurality of summation wavelengths, the slit function for each such product determined by the difference between the first wavelength and the summation wavelength for the respective product, the detected radiant power for each product determined by the summation wavelength for the respective product;

(e) selecting a constant such that the result of step (d) scaled by the constant is equal to the detected radiant power at the second wavelength;

(f) selecting a second plurality of summation wavelengths over a range of wavelengths including at least the interval of significant detected radiant power, but not including wavelengths within a predetermined interval around the first wavelength;

(g) summing the products of the slit function and the detected radiant power spectrum for the second plurality of summation wavelengths, the slit function for each such product determined by the difference between the first wavelength and the summation wavelength for the respective product, the detected radiant power spectrum for each such product determined by the summation wavelength for the respective product; and (h) scaling the result of step (g) by the constant to determine stray light.

9. The method of claim 8 wherein the spectrophotometer includes sample receiving means adapted to receive a sample such that the sample is in the optical path, and wherein step (a) comprises measuring the detected radiant power spectrum with a sample in the optical path such that the detected radiant power spectrum includes a detected radiant power at the first wavelength.

10. The method of claim 9 further including (i) subtracting the stray light determined by step (h) from the detected radiant power at the first wavelength to determine a detected radiant power at the first wavelength compensated for stray light;

(j) measuring a detected radiant power without a sample in the optical path at the first wavelength; and (k) dividing the result of step (i) by the result of step (j) to determine sample transmittance at the first wavelength corrected for stray light.

11. A method for compensating sample transmittance at a first wavelength for stray light in a spectrophotometer where the spectrophotometer has an optical path including a monochromator generating an output beam having an adjustable central wavelength, a detector positioned to receive radiant power from the monochromator, and means for substantially limiting detector response to radiation having wavelengths within an interval of significant detected radiant power, the interval of significant detected radiant power including the first wavelength, the method comprising the steps of determining a reference detected radiant power with the central wavelength at the first wavelength without the sample in the optical path;

determining a second detected radiant power with the central wavelength at the first wavelength with the sample in the optical path;

determining a third detected radiant power with the central wavelength at a second wavelength outside the interval of significant detected radiant power with the sample in the optical path; and subtracting the third detected radiant power from the second detected radiant power and determining the ratio of the result to the reference detected radiant power to determine sample transmittance corrected for stray light.

12. A method for compensating sample transmittance at a first wavelength for stray light in a spectrophotometer where the spectrophotometer has an optical path including a monochromator generating an output beam having an adjustable central wavelength, a detector positioned to receive radiant power from the monochromator, the method comprising the steps of (a) substantially limiting detector response to radiation having wavelengths within an interval of significant detected radiant power, the interval of significant detected radiant power including the first wavelength;
(b) determining a reference detected radiant power with the central wavelength at the first wavelength without the sample in the optical path;
(c) determining a second detected radiant power with the central wavelength at the first wavelength with the sample in the optical path;
(d) determining a third detected radiant power with the central wavelength at a second wavelength outside the interval of significant detected radiant power with the sample in the optical path; and
(e) subtracting the third detected radiant power from the second detected radiant power and determining the ratio of the result to the reference detected radiant power.

13. The method of claim 12 wherein step (a) includes limiting detector response by means of a blocking filter.

* * * * *